US012807910B2

(12) United States Patent
Takeuchi et al.

(10) Patent No.: US 12,807,910 B2
(45) Date of Patent: Nov. 24, 2026

(54) DEVICE FOR FORMING THREE-DIMENSIONAL MUSCLE TISSUE AND METHOD OF PRODUCING THREE-DIMENSIONAL MUSCLE TISSUE

(71) Applicant: NISSIN FOODS HOLDINGS CO., LTD., Osaka (JP)

(72) Inventors: Shoji Takeuchi, Tokyo (JP); Yuya Morimoto, Tokyo (JP); Ai Shima, Tokyo (JP); Yasuaki Ishii, Tokyo (JP); Yusuke Hirata, Tokyo (JP)

(73) Assignee: NISSIN FOODS HOLDINGS CO., LTD., Osaka (JP)

(*) Notice: Subject to any disclaimer, the term of this patent is extended or adjusted under 35 U.S.C. 154(b) by 786 days.

(21) Appl. No.: 18/245,455

(22) PCT Filed: Sep. 2, 2021

(86) PCT No.: PCT/JP2021/032244
§ 371 (c)(1),
(2) Date: Mar. 15, 2023

(87) PCT Pub. No.: WO2022/059498
PCT Pub. Date: Mar. 24, 2022

(65) Prior Publication Data

US 2024/0026260 A1 Jan. 25, 2024

(30) Foreign Application Priority Data

Sep. 15, 2020 (JP) ................................ 2020-154316

(51) Int. Cl.
*C12M 3/00* (2006.01)
*C12M 1/00* (2006.01)

(52) U.S. Cl.
CPC ............ *C12M 21/08* (2013.01); *C12M 23/40* (2013.01)

(58) Field of Classification Search
None
See application file for complete search history.

(56) References Cited

U.S. PATENT DOCUMENTS

2008/0261306 A1 10/2008 Neumann
2012/0035742 A1* 2/2012 Vunjak-Novakovic ...................... C12M 29/10 435/174

(Continued)

FOREIGN PATENT DOCUMENTS

JP 2010-539935 A 12/2010
JP 2018-000194 A 1/2018

(Continued)

OTHER PUBLICATIONS

Ishii et al., "Centimeter-sized Tissue with Perfusable Channels Toward Cultured Steak," *23rd International Conference on Miniaturized Systems for Chemistry and Life Sciences*, pp. 322-323 (Oct. 8, 2019).

(Continued)

*Primary Examiner* — Holly Kipouros
(74) *Attorney, Agent, or Firm* — Leydig, Voit & Mayer, Ltd.

(57) ABSTRACT

The present inventors succeeded in culturing thick three-dimensional muscle tissue in which the muscle fibers are oriented in the same direction by providing channels for transporting a culture medium inside a hydrogel containing skeletal myoblasts. The three-dimensional muscle tissue produced according to the invention is expected to have a steak-like texture. Additionally, in regenerative medicine applications, damage in extensive and thick muscle tissue is expected to be healed with a single treatment by using thick three-dimensional muscle tissue.

4 Claims, 25 Drawing Sheets

(56) References Cited

U.S. PATENT DOCUMENTS

| | | | | |
|---|---|---|---|---|
| 2017/0274121 | A1* | 9/2017 | Takeuchi | C12M 21/08 |
| 2018/0355308 | A1 | 12/2018 | Matsusaki et al. | |
| 2022/0169962 | A1 | 6/2022 | Takeuchi et al. | |

FOREIGN PATENT DOCUMENTS

| | | | |
|---|---|---|---|
| JP | 6427836 | B2 | 11/2018 |
| JP | 2019-122335 | A | 7/2019 |
| WO | WO 2020/179257 | A1 | 9/2020 |

OTHER PUBLICATIONS

Ishii et al., "Centimeter-sized Tissue with Perfusable Channels Toward Cultured Steak," *23rd International Conference on Miniaturized Systems for Chemistry and Life Sciences* (Oct. 30, 2019).
Ishii et al., "Formation of Micro-size Perfusable Channels in Mm-thick Muscle Tissue," *33rd IEEE International Conference on MENS* (Jan. 19, 2020).
Ishii et al., "Formation of Micro-size Perfusable Channels in MM-thick Muscle Tissue," IEEE MEMS 2020, pp. 456-458 (2020).
Japan Patent Office, International Search Report in International Patent Application No. PCT/JP2021/032244 (Nov. 16, 2021).
Furuhashi, "The Cutting Edge of Alternative Meat," Japanese Journal of Meat Science and Technology, 61(1):43-48 (2020).
Japan Patent Office, Office Action in Japanese Patent Application No. 2022-550456 (Jan. 6, 2026).

* cited by examiner (A)

(B)

(C)

(A)

(B)

DEVICE FOR FORMING THREE-DIMENSIONAL MUSCLE TISSUE AND METHOD OF PRODUCING THREE-DIMENSIONAL MUSCLE TISSUE

TECHNICAL FIELD

The present invention primarily relates to a device for constructing a three-dimensional muscle tissue and a method for producing a three-dimensional muscle tissue.

BACKGROUND ART

There is an increasing demand for edible meat due to population growth and rising incomes in emerging countries. However, increasing the meat supply is difficult due to soaring prices of grains for livestock feed and problems in securing breeding places. The development of meat alternatives has thus been hoped for.

Cultured meat is produced by forming tissue using skeletal muscle cells proliferated in culture. Since production is possible in a laboratory, production that is not affected by climate change is possible. Additionally, greenhouse gas emissions are low, and the environmental impact is small, compared to conventional animal husbandry.

CITATION LIST

Patent Literature

PTL 1: JP2018-000194A
PTL 2: JP6427836B

SUMMARY OF INVENTION

Technical Problem

For producing edible meat with a steak-like texture from cells, construction of cultured meat in which the direction of muscle fibers is well oriented (referred to below as "three-dimensional muscle tissue") is necessary. However, conventional techniques only provide minced meat, in which the direction of muscle fibers is not well oriented. Although three-dimensional muscle tissues obtained using human or mouse skeletal muscle cells have been reported in the field of regenerative medicine, the tissues do not have sufficient thickness (Patent Literature (PTL) 1 and PTL 2).

An object of the present invention is to provide a device for constructing a three-dimensional muscle tissue for producing a three-dimensional muscle tissue, and a method for producing a three-dimensional muscle tissue.

Solution to Problem

The present invention provides the following device for constructing a three-dimensional muscle tissue and method for producing a three-dimensional muscle tissue.

[1]

A device for constructing a three-dimensional muscle tissue, comprising a culture tank having a culture space, a first connector and a second connector provided at positions opposite to each other within the culture space, a culture medium inlet provided at the first connector, a plurality of first support members that are provided at the first connector and from which culture medium introduced from the culture medium inlet is enabled to be discharged, a plurality of second support members that are provided at the second connector and into which culture medium is enabled to flow, a first muscle tissue anchor engaged to the first support members and/or the first connector, and a second muscle tissue anchor engaged to the second support members and/or the second connector.

[2]

The device for constructing a three-dimensional muscle tissue according to Item [1], further comprising channel-forming members for culture medium that are engaged to the first support members and the second support members.

[3]

The device for constructing a three-dimensional muscle tissue according to Item [1] or [2], further comprising a pump for supplying culture medium to the culture medium inlet.

[4]

A method for producing a three-dimensional muscle tissue, the method comprising, in the device for constructing a three-dimensional muscle tissue of any one of Items [1] to [3], filling the culture space between the first connector and the second connector with a hydrogel containing skeletal myoblasts, with the channel-forming members being inserted into the first support members and the second support members, removing the channel-forming members after the hydrogel is solidified, and supplying culture medium from the culture medium inlet through the first support members to the second support members to three-dimensionally culture the skeletal myoblasts.

[5]

A three-dimensional muscle tissue comprising a plurality of channels capable of transporting culture medium, and muscle fibers oriented in the same direction (with the proviso that heme is not included in the three-dimensional muscle tissue).

[6]

The three-dimensional muscle tissue according to Item [5], wherein the interval between adjacent channels is 500 to 1500 μm.

[7]

The three-dimensional muscle tissue according to Item [5] or [6], wherein the direction of orientation of the channels and the direction of orientation of the muscle fibers are approximately parallel.

[8]

The three-dimensional muscle tissue according to any one of Items [5] to [7], which does not substantially comprise heme.

Advantageous Effects of Invention

The present invention provides, in particular, a device for constructing a three-dimensional muscle tissue and a production method. The device etc. of the present invention enable production of three-dimensional muscle tissue with sufficient thickness. Thus, the three-dimensional muscle tissue produced according to the present invention can be expected to have a steak-like texture. Additionally, in regenerative medicine applications, damage in extensive and thick muscle tissue is expected to be healed with a single treatment by using thick three-dimensional muscle tissue.

DESCRIPTION OF EMBODIMENTS

Figure 1:
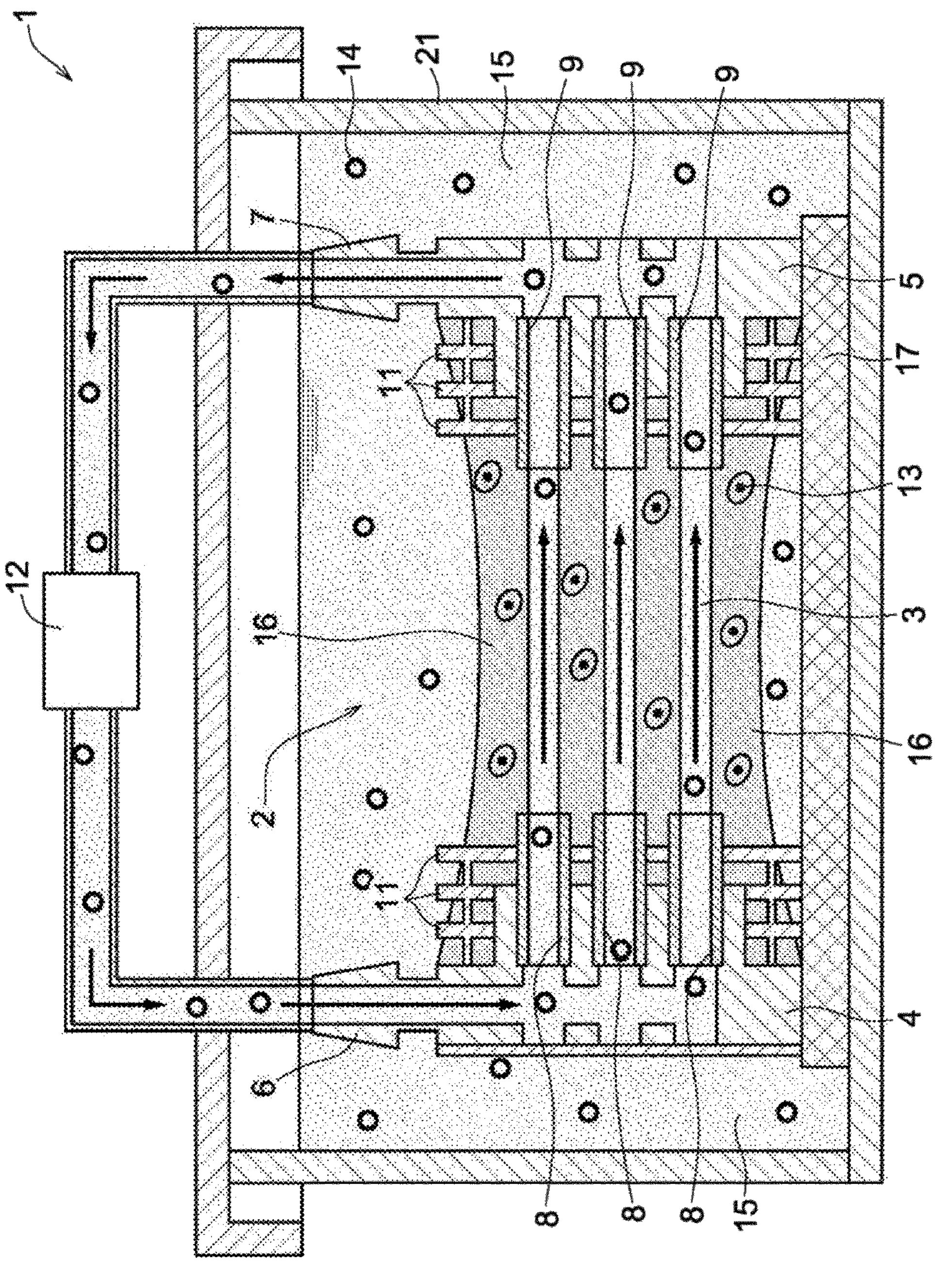
FIG. 1 is a schematic diagram showing the outline of the device for constructing a three-dimensional muscle tissue according to the present invention.
Figure 2:
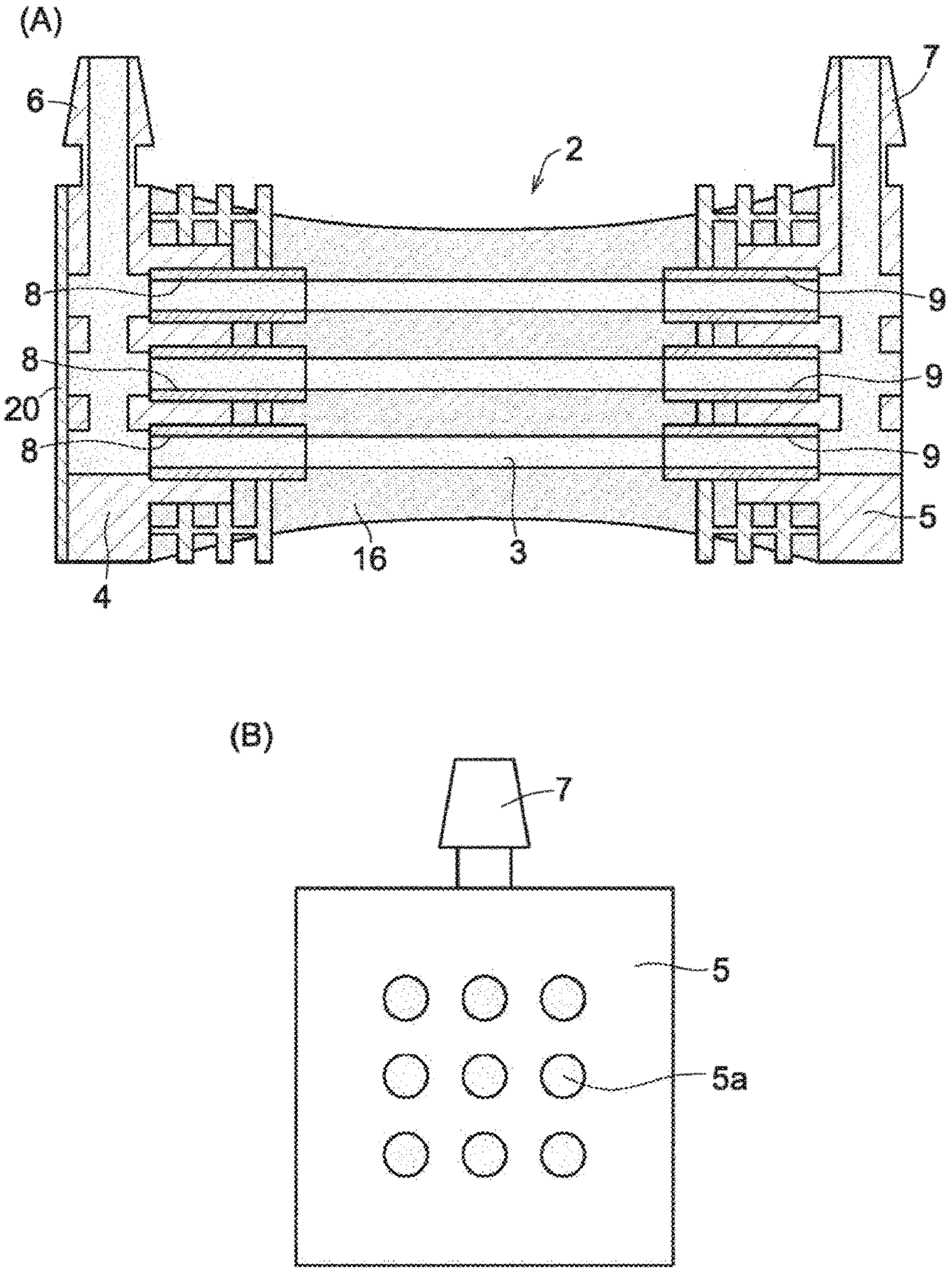
FIG. 2 shows one embodiment of the device for constructing a three-dimensional muscle tissue according to the present invention.

FIGS. 1 and 2 are schematic diagrams showing one embodiment of the device for constructing a three-dimensional muscle tissue according to the present invention.

The device 1 for constructing a three-dimensional muscle tissue of the present invention comprises a first connector 4 and a second connector 5, which are provided opposite to each other, and channels 3 for culture medium, which are foiled between first support members 8 and second support members 9.

In one embodiment of the present invention, the channels 3 can be famed by filling a culture space 2 between the first connector and the second connector with a hydrogel containing skeletal myoblasts, with solid channel-forming members such as wire or acupuncture needles, being inserted between the first support members 8 and the second support members 9 (FIG. 5(B)), and pulling out the channel-forming members 10 after the hydrogel is solidified. In this case, the channels 3 are cavities famed between the first connector 4 and the second connector 5 in a three-dimensional muscle tissue 16. Since the channel-forming members 10 are pulled out after the hydrogel containing skeletal myoblasts is injected into the culture space, the surface of the channel-forming members 10 is preferably coated with a material that inhibits cell adhesion, such as bovine serum albumin (BSE). At the time of injection, the hydrogel containing skeletal myoblasts has a fluidity that enables injection into the culture space. Then, after a short time, the gel is solidified to acquire sufficient strength and shape retention properties.

In FIG. 1, the holes of the first connector 4, into which the channel-foaming members 10 are inserted, are blocked with a sealing material 20. The holes of the second connector 5, into which the channel-forming members 10 are inserted, are open. The holes of the second connector 5, into which the channel-forming members 10 are inserted, may also be blocked with the sealing material 20 in the same manner. The first connector 4 and the sealing material 20 may be formed as a single unit. Even when the first connector 4 and the sealing material 20 are famed as a single unit, no particular problem is caused as long as a culture medium can be circulated. In another embodiment of the present invention, the channels 3 may be formed by attaching hollow channel-forming members 10, which are formed so that gaseous components such as oxygen and carbon dioxide and/or nutrients 14 (referred to below as "the nutrients etc. 14") and/or waste can permeate, between the first support members 8 and the second support members 9. By allowing a culture medium 15 to flow inside the channel-forming members 10, the nutrients etc. 14 can be supplied to the interior of the three-dimensional muscle tissue, and carbon dioxide and waste can be discharged. The channels 3 for the culture medium 15 here are cavities present inside the channel-forming members 10. The hollow channel-foaming members 10 when included in the device during culture of skeletal myoblasts 13 must be removed at the end of culture or must be formed of a material that does not cause an adverse effect (e.g., cultured blood vessels) even when left in the device.

The culture medium 15 is supplied by a pump 12 to a culture medium inlet 6 and allowed to flow from the first support members 8 through the channels 3 to the second support members 9. The culture medium 15 containing waste after passing through the second support members 9 is discharged from a culture medium outlet 7 famed at the second connector 5. Each of the first support members 8 and the second support members 9 has an opening into which the channel-forming member 10 is inserted. The sealing material 20 is for sealing the openings on the side of the first support members. The sealing material 20 allows the culture medium 15 introduced from the culture medium inlet 6 to flow through the channels 3 in the direction of the arrows in FIG. 1. Examples of the sealing material 20 include Ecoflex (registered trademark) produced by BASF. In FIGS. 1 and 2, openings 5*a* on the side of the second support members are not sealed; thus, the culture medium from the second support members 9 is partly discharged directly from the culture medium outlet 7, and partly mixed with the culture medium 15 outside the culture space and then discharged from the culture medium outlet 7. The openings on the side of the second support members 8 may also be sealed with the sealing material 20. In one embodiment, the culture medium may be discharged from the culture medium outlet 7. In another embodiment, the tip of a tube for discharge may be disposed within the culture medium outside the muscle tissue 16 so that the culture medium outside the muscle tissue is mixed with the culture medium containing waste that has passed through the channels 3, and the resulting mixed culture medium is discharged.

The surface of the cultured product of the skeletal myoblasts 13 (three-dimensional muscle tissue 16) is well supplied with the nutrients etc. 14 from the culture medium 15, the interior of the muscle tissue 16 is supplied with the nutrients etc. 14 from a fresh culture medium flowing through the channels 3, and a waste liquid with high concentrations of carbon dioxide and waste is discharged from the culture medium outlet 7. In FIG. 1, the culture medium is circulated; however, the culture medium discharged from the culture medium outlet may be discarded, and a fresh culture medium may be supplied from the culture medium inlet 6 by a pump 12. Examples of pumps for use include syringe pumps. The pump 12 may be connected to the culture medium inlet 6 and the culture medium outlet 7 via a tube. The system of the present invention may be equipped with electrodes (not shown). Stimulation of myoblasts or muscle tissues by electrodes can promote the construction of a muscle tissue. The culture medium 15 may be circulated when a sufficient amount of the culture medium 15 is present in the culture tank; however, when a small amount of the culture medium 15 is present, the old culture medium 15 that has passed through the channels 3 is preferably discarded.

The first support members and the second support members are preferably disposed in a straight line so as to form straight channels. The interval between adjacent channels depend on the thickness (diameter or cross-sectional area) of the channels, but is preferably about 500 to 1500 μm.

As shown in the cross-sectional views in FIGS. 3(A) and (B), the skeletal myoblasts 13 proliferate in an excellent manner in the periphery of the muscle tissue 16 since the nutrients etc. 14 are well supplied from the culture medium 15. However, the supply of the nutrients etc. 14 is not sufficient in the interior of the muscle tissue 16; thus, the thicker and more filling the muscle tissue 16 is, the more likely it is to cause necrosis of the cultured cells. In the present invention, the nutrients etc. 14 are evenly supplied to the periphery and interior of the muscle tissue 16, and carbon dioxide and waste are discharged; thus, a thick muscle tissue 16 can be obtained in a short period of time, and no issue is caused by a difference between the surface and interior of the muscle tissue 16.

Figure 3:
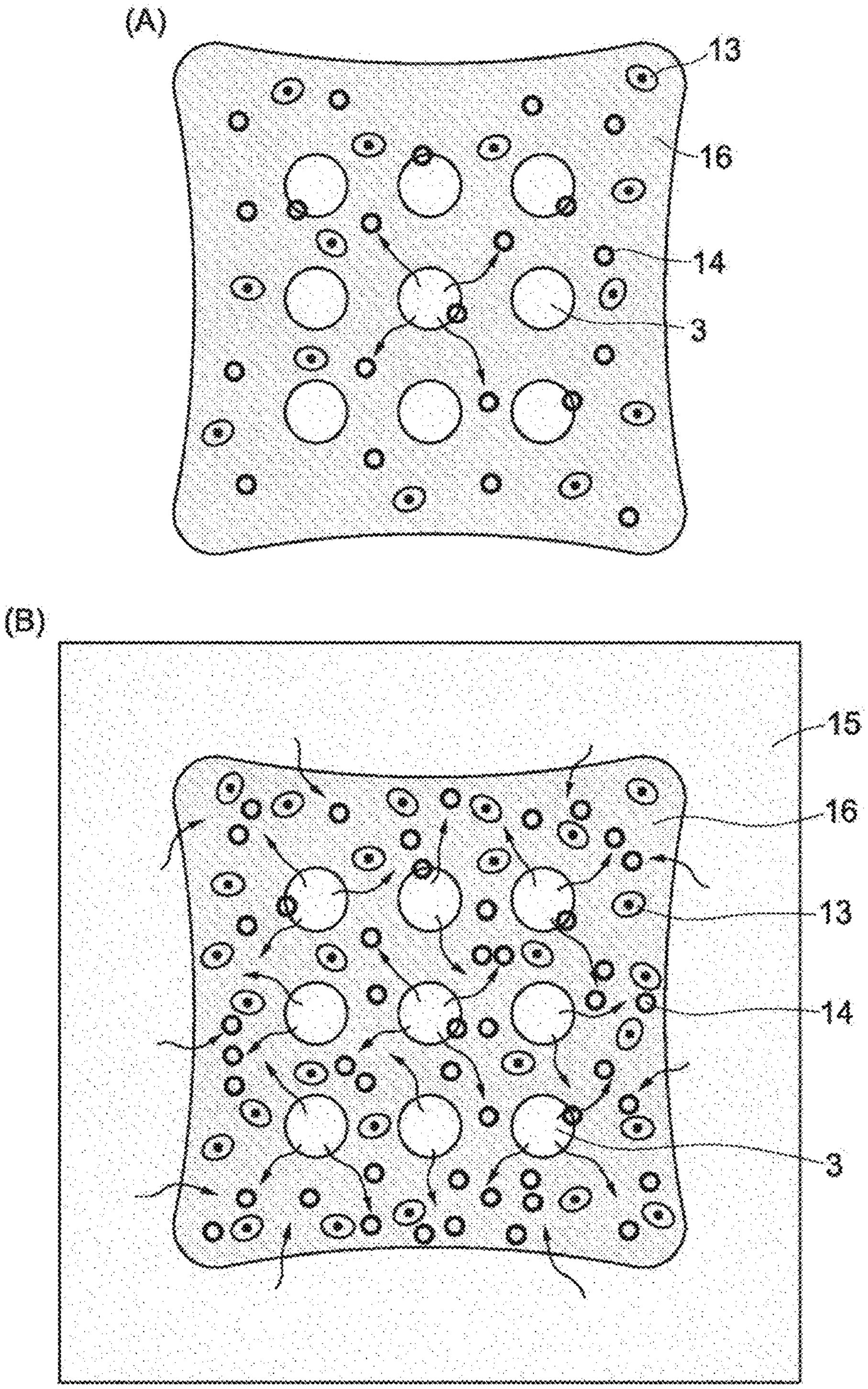
FIG. 3(A) is a schematic cross-sectional view showing a three-dimensional muscle tissue in culture.
FIG. 3(B) is a schematic cross-sectional view showing a three-dimensional muscle tissue in culture.

The first and second muscle tissue anchors 11 may have any shape, and preferably have a mesh-like shape as shown in FIGS. 4(A) to (C). The muscle tissue 16 is entangled in the mesh-like anchors 11 and fixed at both ends. The skeletal myoblasts 13 undergo shrinkage when culture is continued. However, being fixed by the anchors 11 on both sides, the thick muscle tissue 16 can be maintained even when culture is continued. In FIGS. 1 to 3, the muscle tissue is slightly concave at around the center since the skeletal myoblasts 13 undergo shrinkage when culture is continued.

Electrical stimulation may be applied during culture of the muscle tissue 16 to promote proliferation of the skeletal myoblasts 13.

Figure 5:
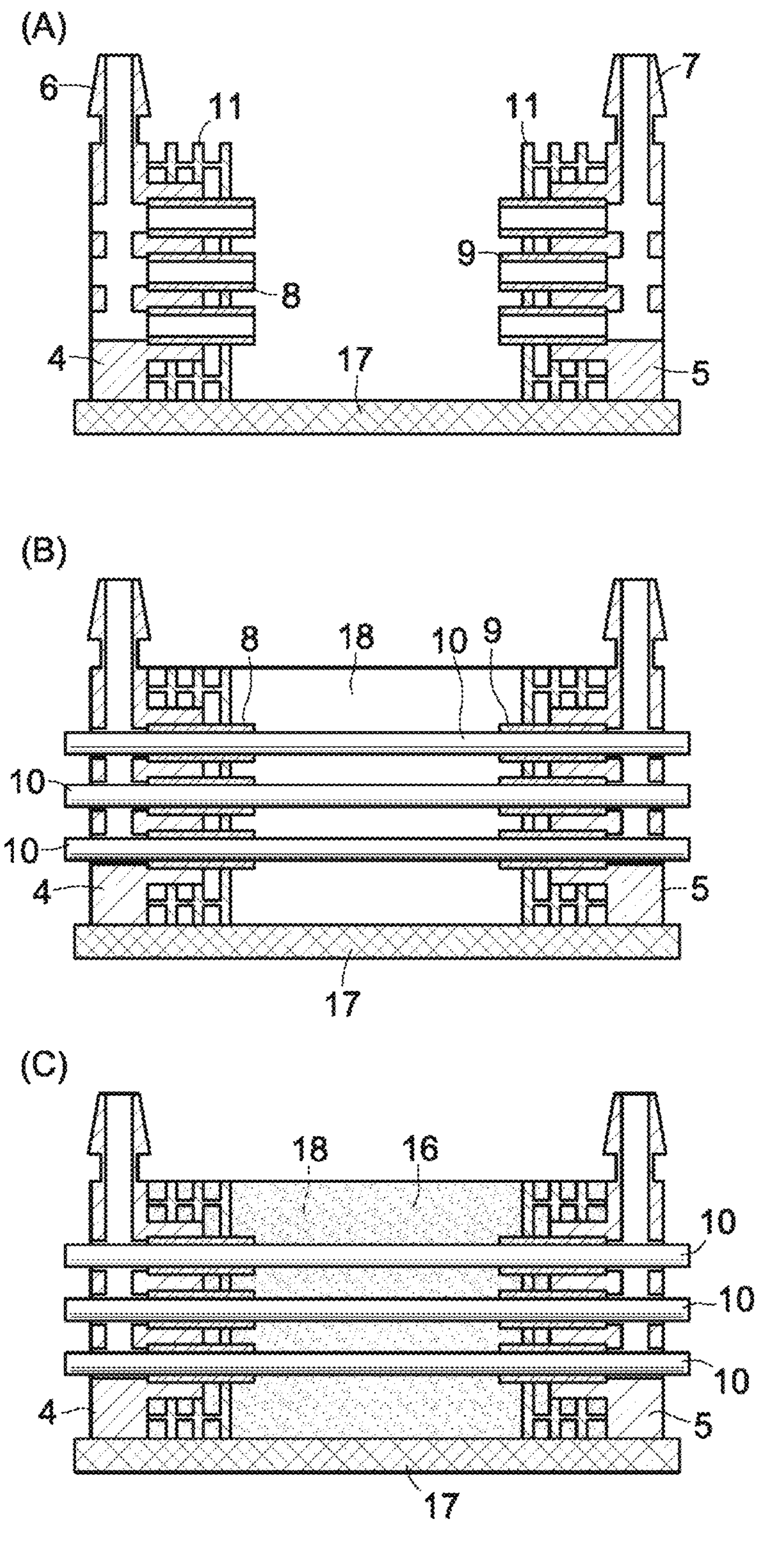
FIG. 5 is schematic diagrams showing support members with anchors.
Figure 6:
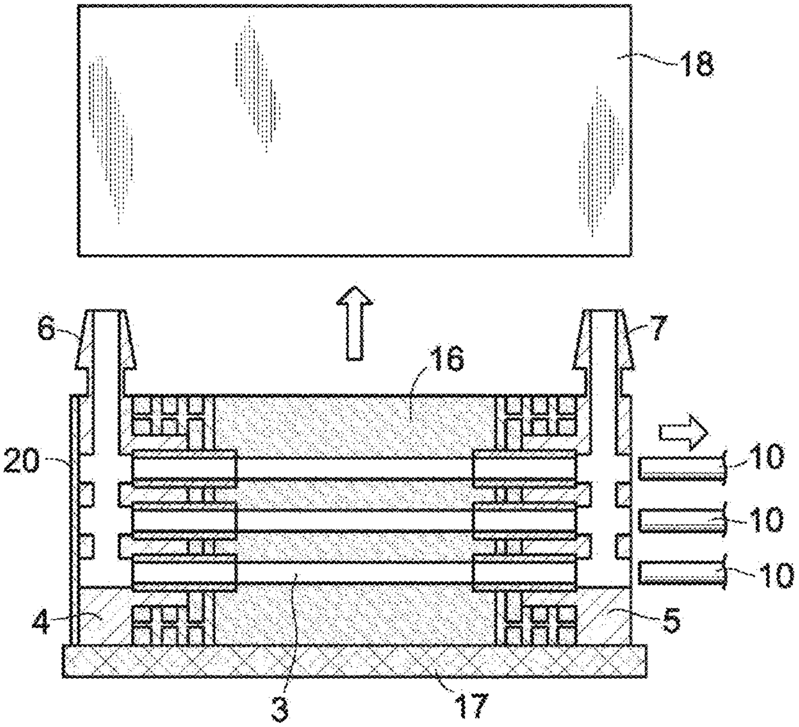
FIG. 6 shows a process for forming a device for constructing a three-dimensional muscle tissue at the time of parallel culture.
Figure 6:
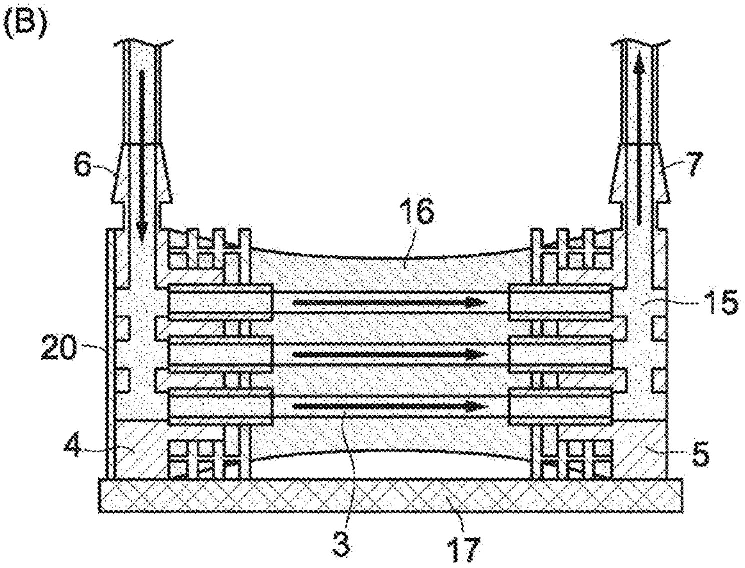

FIGS. 5 and 6 show the outline of the process of the method for producing a three-dimensional muscle tissue of the present invention. In FIG. 5(A), the first connector 4, the second connector 5, and the muscle tissue anchors 11 are fixed to a substrate 17. In FIG. 5(B), the channel-forming members 10 are inserted into the first support members 8 and the second support members 9, and two side walls 18 are fixed at the front and rear sides of the substrate 17 to form the culture space 2. FIG. 5(C) is a diagram in which the culture space 2 is filled with a hydrogel containing the skeletal myoblasts 13.

FIG. 6(A) shows the state in which the channel-forming members 10 have been pulled out, and the two front and rear side walls 18 have been removed. Subsequently, in FIG. 6(B), a culture medium is allowed to flow from the culture medium inlet 6 towards the culture medium outlet 7 to start culture. A hydrogel containing the skeletal myoblasts 13 is injected into the gap in the culture space 2 accommodating the muscle tissue anchors 11, the first support members 8, the second support members 9, the channel-forming members 10, and the like. After standing still for a while, the gel is solidified, and the shape is retained. Then, the side walls 18 are removed. The time required for the gel to solidify must be appropriately adjusted since it depends on the type of the hydrogel and the environment. As a guide, for example, collagen gel requires about 30 minutes, and matrigel requires about 12 hours.

Figure 7:
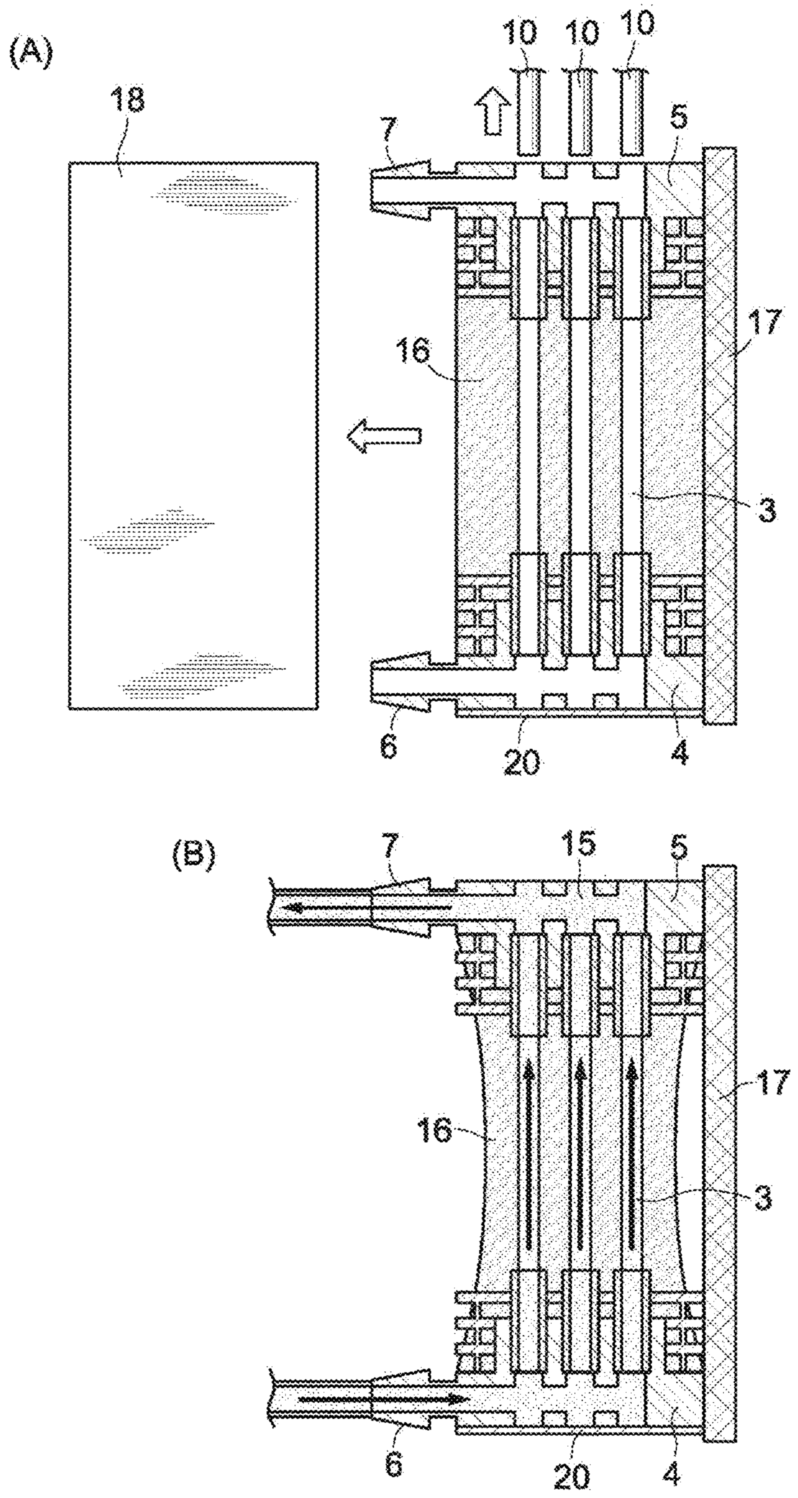
FIG. 7 shows a process for forming a device for constructing a three-dimensional muscle tissue at the time of vertical culture.

FIG. 6 is diagrams in which a culture medium is allowed to flow in the horizontal direction, and FIG. 7 is diagrams in which a culture medium is allowed to flow in the vertical direction. The embodiment shown in FIG. 7, which does not suffer from the risk of narrowing the channels due to the action of gravity on the muscle tissue, is preferable.

In one preferable embodiment of the present invention, the oxygen concentration in the culture medium is preferably 80% or more of the saturated oxygen concentration.

The muscle tissue anchors may be coated with a biocompatible material to improve adhesion of skeletal myoblasts and prevent the muscle tissue from falling off during culture. Examples of the biocompatible material include fibronectin.

According to the culture method of the present invention, myotubes are formed when the culture of skeletal myoblasts is continued.

The hydrogel for use in culture of skeletal myoblasts may be a hydrogel of fibrin, fibronectin, laminin, collagen (e.g. types I, II, III, V, and XI), agar, agarose, a glycosaminoglycan, hyaluronic acid, a proteoglycan, and other components constituting an extracellular basement membrane matrix. The hydrogel for use may also be a commercial product. Examples include components based on a mouse EHS tumor extract (containing type IV collagen, laminin, heparan sulfate proteoglycan, etc.) sold under the trade name "Matrigel."

As used herein, the term "collagen" encompasses undenatured collagen and denatured collagen. Examples of denatured collagen include gelatin.

The hydrogel preferably contains collagen, preferably undenatured type I collagen, in particular, when the skeletal myoblasts are derived from a bovine. The content of type I collagen, when contained, is preferably 0.3 mg/mL or more, more preferably 1.0 to 3.0 mg/mL, and still more preferably 1.0 to 1.5 mg/mL.

In terms of the skeletal myoblasts in the hydrogel, for example, the cell concentration is about $1.0\times10^6$ cells/ml or more, preferably about $1.0\times10^7$ cells/ml to about $1.0\times10^8$ cells/ml, and more preferably $5.0\times10^7$ cells/ml to about $1.0\times10^8$ cells/ml.

The skeletal myoblasts in the hydrogel can be prepared according to known methods. For example, primary myoblasts obtained by subjecting biological muscle tissue to degradative enzyme (e.g., collagenase) treatment may be used. Primary myoblasts are preferably filtered to remove impurities, such as connective tissue.

The skeletal myoblasts for use may also be cells induced to differentiate from stem cells with pluripotency, such as ES cells and iPS cells, or from somatic stem cells with an ability to differentiate into skeletal myoblasts.

Skeletal myoblasts are derived from vertebrates, such as mammals, birds, reptiles, amphibians, and fish species. Examples of mammals include non-human mammals, such as monkeys, bovines, horses, pigs, sheep, goats, dogs, cats, guinea pigs, rats, and mice. Examples of birds include ostriches, chickens, ducks, and sparrows. Examples of reptiles include snakes, crocodiles, lizards, and turtles. Examples of amphibians include frogs, newts, and salamanders. Examples of fish species include salmon, tuna, sharks, sea bream, and carp. When the three-dimensional muscle tissue is for edible use, skeletal myoblasts are preferably derived from mammals bred for animal husbandry, such as bovines, pigs, sheep, goats, and horses, and more preferably derived from a bovine.

The skeletal myoblasts for use may be skeletal myoblasts that have been genetically modified by homologous recombination, CRISPR/Cas9, or other genome editing methods, or skeletal myoblasts that have not been genetically modified. In one embodiment of the case in which the three-dimensional muscle tissue is for edible use, the skeletal myoblasts for use are preferably non-genetically modified skeletal myoblasts, from the standpoint of safety and consumer preference.

The culture medium may contain medium components (e.g., various amino acids, inorganic salts, and vitamins), serum components (e.g., growth factors, such as IGF-1, bFGF, insulin, and testosterone), antibiotics, and the like.

In the present invention, a three-dimensional muscle tissue primarily refers to an artificially produced muscle that is not derived from organisms. The three-dimensional muscle tissue of the present invention is formed of skeletal muscle cells (striated muscle cells). Skeletal muscle cells are in the foam of myotubes (myotube cells) or muscle fibers obtained through multinucleation of their precursors, i.e., myoblasts.

Typically, muscle fibers contain as a constituent unit myofibrils composed of filaments of actin, which is a protein of muscle (actin filaments), and filaments of myosin, which is a protein of muscle (myosin filaments). Myofibrils have a structure in which multiple sarcomere structures are repeated in the long-axis direction. Contraction and relaxation of muscles are known to occur based on the interaction (sliding) between actin and myosin in sarcomeres.

The three-dimensional muscle tissue of the present invention preferably has a sarcomere structure. However, no limitation is imposed on whether sliding occurs in the sarcomere structure.

Whether the three-dimensional muscle tissue has a sarcomere structure can be evaluated by known techniques. For example, the presence of sarcomeric α-actinin (SAA), which is a protein of the Z-membrane of the sarcomere structure, is evaluated by SAA immunostaining. When the SAA immunostaining is positive, and when SAA is distributed in regular stripes, the muscle tissue can be determined to have a sarcomere structure.

In the three-dimensional muscle tissue of the present invention, the muscle fibers are aligned and oriented in the same direction. The orientation of muscle fibers can be evaluated, for example, by SAA immunostaining.

When the three-dimensional muscle tissue of the present invention is for edible use, the components (preferably all components) for use in the production method of the present invention are preferably, but not limited to, components that satisfy predetermined standards and whose safety is ensured for production of food and/or for edible use.

The culture of skeletal myoblasts can be performed, for example, in the medium for proliferation culture described above by techniques known to those skilled in the art. For example, culture may be suitably performed under conditions of about 37° C. and a carbon dioxide concentration of about 5 to 10% (v/v). However, the technique is not limited to this. The culture under such conditions can be performed, for example, in a known CO 2 incubator.

The culture medium for proliferation culture may be a medium obtained by supplementing a general-purpose liquid medium, such as Dulbecco's modified Eagle's medium (DMEM), Eagle's minimal essential medium (EMEM), or alpha modified minimum essential medium (αMEM) with a serum component (e.g., horse serum, fetal bovine serum (FBS), or human serum), a component such as a growth factor, and an antibiotic such as penicillin or streptomycin.

When a serum component is added to the medium for proliferation culture, fetal bovine serum may be used as the serum component. The concentration of the serum component may be about 10% (v/v).

The culture duration may be, for example, about 1 day to 2 weeks.

The production method of the present invention can induce differentiation of skeletal myoblasts into myotubes. This differentiation induction causes multinucleation of skeletal myoblasts through cell fusion with surrounding cells to form myotubes. The myotubes further mature to form muscle fibers.

The culture above can be performed, for example, by a technique known to those skilled in the art in a medium for induction of differentiation (medium for multinucleation). For example, culture may be suitably performed under conditions of about 37° C. and a carbon dioxide concentration of about 5 to 10% (v/v). However, the technique is not limited to this. The culture under such conditions can be performed, for example, in a known $CO_2$ incubator.

When nutrients are scarce, myoblasts are known to undergo multinucleation while engulfing surrounding cells. Thus, induction of differentiation into myotubes is preferably performed in a medium with fewer nutrients than the medium used for the proliferation culture. Horse serum, which is known to contain fewer nutrients than fetal bovine serum, may be used. The concentration of the serum component may be about 2% (v/v).

As shown in FIGS. 6 and 7, the channels in which the culture medium flows may be in the horizontal or vertical direction. The channels are preferably in the vertical direction, which can prevent channels from being narrowed by their own weight.

The three-dimensional muscle tissue of the present invention does not necessarily contain heme. According to the present invention, heme is not required to supply oxygen to the cells. Heme that is slightly incorporated during cell harvesting or that is added for coloring or flavoring, rather than for oxygen supply, is regarded as an additive and is not regarded as heme in the present invention.

EXAMPLES

The present invention is described in more detail below with reference to Examples; however, the invention is, of course, not limited to the following Examples.

Example 1

(I) Creation of Support Members with Anchors

As shown in FIGS. 4(A) to (C), support members 8 or 9 and a muscle tissue anchor 11 were vertically disposed in a mesh foam with three rows to create support members with anchors.

The muscle tissue anchors 11 as used here fix a shrinking muscle tissue. The support members 8 and 9 supply nutrition to the interior of the muscle tissue through a culture medium. A first connector 4 and a second connector 5 fix the muscle tissue anchor 11 and the first support members 8 or the second support members 9.

As shown in FIGS. 1 and 6, the holes of the first connector 4, into which channel-forming members 10 were inserted, were blocked with a sealing material 20 (Ecoflex (registered trademark), produced by BASF). However, the holes of the second connector 5, into which the channel-foaming members 10 were inserted, were open to thus allow a culture medium passed through the channels to be mixed with the culture medium in the culture space and discharged from the culture medium outlet.

Figure 4:
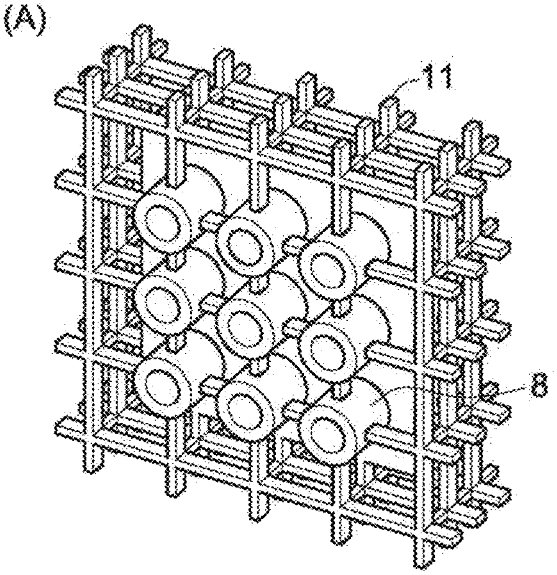
FIG. 4 is a partial perspective view showing a first connector, a culture medium inlet, a muscle tissue anchor, and first support members.
Figure 4:
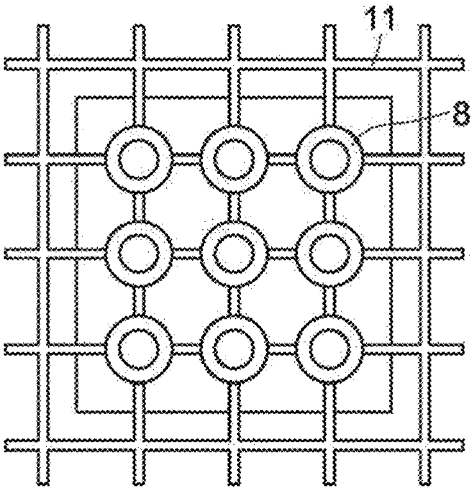
Figure 4:
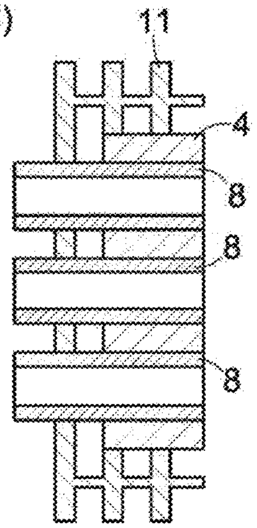

The support members with anchors shown in FIG. 4 were produced using a stereolithography apparatus (Digital Wax 028J, DWS). For the DWS, the dedicated resin for the DWS (DM210) was used.

(II) Injection of Hydrogel Containing Skeletal Myoblasts (C2C12) into a Device and Culture (Parallel Culture or Vertical Culture)

As shown in FIG. 5(B), acupuncture needles as the channel-forming members 10 were inserted between the first support members 8 and the second support members 9. Further, side walls 18 were provided at the front and rear sides of the device to form a culture space 2. In this state, a hydrogel containing skeletal myoblasts was injected into the device.

The muscle tissue anchors 11, the first support members 8, and the second support members 9 were coated with PMBV631 (2 wt % ethanol), followed by coating overnight with fibronectin (10 µL), which promotes cell adhesion. The acupuncture needles were coated by immersion in bovine serum albumin (BSA, 1%) for 1 hour to inhibit cell adhesion. For cells, C2C12 myoblasts were used. The cells ($2.0\times10^6$) seeded in a 150-mm dish and passaged after 2 days were used as the cells; the cells were all P11 (passaged 11 times) or less. The cell concentration was $4.0\times10^7$ cells/ml.

In parallel culture, a hydrogel of 100% collagen gel (I-AC, AteloCell) was used, and in vertical culture, a hydrogel of a mixture of matrigel (Matrigel, Corning) and the collagen gel in a ratio of 1:1 (weight ratio), or a hydrogel of 100% matrigel was used.

The hydrogel containing skeletal myoblasts (C2C12) was injected into the device as follows.

After 3 mL of trypsin was added to a dish in which C2C12 was proliferated, incubation was performed at 37° C. for 5 minutes, and the cells were detached from the dish. After 7 mL of Dulbecco's modified Eagle's medium (below, "DMEM") was added to the dish, pipetting was performed twice with an electric pipette to collect in 50 mL tube. Centrifugation was performed for 3 minutes (200 g) to precipitate the cells. Subsequent operations were conducted on ice.

A specific process for parallel culture is described below. Parallel culture refers to culture performed by disposing channels 3 perpendicular to the direction of gravity.

1. Two support members with anchors are positioned opposite to each other, and a first connector 4 and a second connector 5 are fixed to a substrate 17.
2. Acupuncture needles (SJ-217, produced by Seirin Corporation) are inserted into the first support members and the second support members, and side walls 18 are attached to the substrate 17 to form a culture space 2.
3. A hydrogel containing C2C12 is injected into the culture space, and incubation is performed at 37° C. for 30 minutes to solidify the hydrogel.
4. The device obtained in step 3 is placed in a 25-mL tube, and the device is immersed in a culture medium and allowed to stand for 30 minutes.
5. The acupuncture needles are removed to form channels 3.
6. The device obtained in step 5 is transferred to a dish, and the side walls 18 are removed.
7. The holes for needle insertion on the side of a culture medium inlet 6 are blocked with a sealing material 20.
8. One perfusion tube is connected to the culture medium inlet 6, and the other perfusion tube is placed near the liquid surface to perfuse the culture medium. Each of the two perfusion tubes is connected to a syringe pump, and the culture medium is perfused with the syringe pumps.

In step 8 above, the other perfusion tube is inserted below the liquid surface of the culture medium. In another embodiment, the other perfusion tube may be connected to a culture medium outlet 7.

A specific process for vertical culture is described below. Vertical culture refers to culture performed by disposing the channels 3 parallel to the direction of gravity.

1. Two support members with anchors are positioned opposite to each other, and a first connector 4 and a second connector 5 are fixed to a substrate 17.
2. Acupuncture needles (SJ-217, produced by Seirin Corporation) are inserted into the first support members and the second support members, and side walls 18 are attached to the substrate 17 to form a culture space 2.
3. A hydrogel containing C2C12 is injected into the culture space, and incubation is performed at 37° C. for 30 minutes to solidify the hydrogel.
4. One perfusion tube is connected to a culture medium inlet 6.
5. The device obtained in step 4 is placed in a 100-mL tube, and electrodes are brought close to the tube.
6. The 100-mL tube is filled with a culture medium and allowed to stand for 30 minutes.
7. The acupuncture needles are removed to form channels 3.
8. The side walls 18 are removed.
9. The holes for needle insertion on the side of the culture medium inlet 6 are blocked with a sealing material 20.
10. The other perfusion tube is placed near the liquid surface to suck up and perfuse the culture medium. Each of the two perfusion tubes is connected to a syringe pump, and the culture medium is perfused with the syringe pumps.

Figure 8:
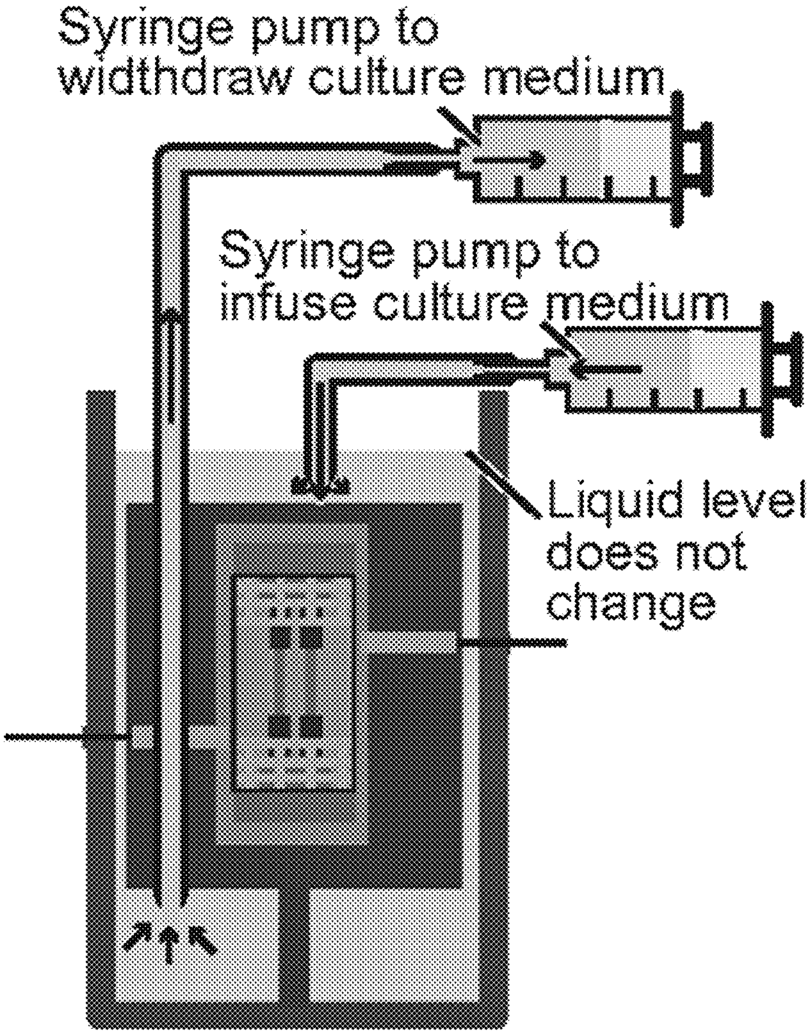
FIG. 8 is a conceptual diagram showing a process of medium replacement without changing the liquid surface level.

The vertical culture was performed by rotating the tube at 60 rpm by shaking the tube with a shaker. By creating convection flows in the culture medium within the tube, the concentration of oxygen, which can only be taken in from the liquid surface of the culture medium, can be kept constant within the culture medium. As shown in FIG. 8, two syringe pumps each connected to a tube may be provided. By placing the tube for medium injection above the liquid surface and the tube for medium suction close to the bottom, and by driving the syringe pumps for suction and injection simultaneously, culture can be performed without changing the liquid surface level of the culture medium.

To promote maturation of myotubes, electrical stimulation of 0.5 V/mm was applied to the cultured product for 2 hours while maintaining the temperature and carbon dioxide concentration in the device constant from day 4 after the start of culture.

After completion of culture, tissue sections of the three-dimensional muscle tissue were created.

The sections were prepared in the following order: (i) cryoprotection treatment, (ii) freeze treatment, (iii) creation of sections, (iv) HE staining, and (v) immunostaining.

(i) Cryoprotection Treatment

Cryoprotection treatment is a treatment for preventing ice grains from being formed in the tissue when frozen. In the following description, PBS refers to phosphate buffered saline.

1. After the cultured product (three-dimensional muscle tissue) was washed once with PBS(−), the culture product was immersed for one day each in cryo-dishes containing a 10% sucrose/PBS(−) solution, 20% sucrose/PBS(−) solution, or 30% sucrose/PBS(−) solution.
2. For the washing treatment and immersion treatment in 10%, 20%, and 30% sucrose/PBS(−) solutions, the three-dimensional muscle tissue detached from the anchors was used.
3. The muscle tissue was immersed in a cryo-dish filled with an OCT compound agent and allowed to stand at room temperature for 2 days.

(ii) Freeze Treatment

Freeze treatment was performed before the creation of frozen sections.

1. Liquid nitrogen was poured into an insulated container (height: 4 to 5 cm).
2. The cryo-dish was placed into the liquid nitrogen by using tweezers.
3. Since long-time immersion in liquid nitrogen causes cracking in the three-dimensional muscle tissue, the cryo-dish was moved in and out of the liquid nitrogen every 1 to 2 seconds to gradually solidify the three-dimensional muscle tissue.

(iii) Creation of Sections

Sections with a thickness of 8 μm were created using a cryostat. The details are described as follows.

1. The cryo-dish containing the three-dimensional muscle tissue sample after freeze treatment was placed in a cryostat and warmed to −20° C.
2. The sample was collected from the cryo-dish, and an 8-μm-thick short-side section was created.
3. The sample was rotated 180° to create an 8-μm-thick short-side section on the opposite side.
4. The sample was rotated 90° to create three to four 8-μm-thick long-side sections.
5. The sample was shaved (200 μm), and long-side sections were repeatedly created until no more long-side sections were created.
6. The resulting sections were attached to MAS-coated glass slides.

(iv) HE staining

HF staining was performed as follows.

1. After the section was prepared, the section was dried for 1 day.
2. The section was immersed in a Mayer's hematoxylin solution and allowed to stand for 5 minutes.
3. Excess hematoxylin solution was removed through adsorption on paper.
4. The section was transferred to a staining bottle containing water to remove excess staining solution.
5. The section was immersed in warm water at 50° C. and allowed to stand for 5 minutes.
6. The section was transferred to a staining bottle containing water.
7. The section was immersed in an eosin solution and allowed to stand for 5 minutes.
8. The slide glass was immersed in 100% ethanol and slowly moved up and down 5 times to remove excess staining solution.
9. The operation in step 8 was performed three times in total using different bottles.
10. The resulting product was immersed in xylene (3 times for 5 minutes each).
11. A few drops of Entellan were added to the section for sealing, and a cover glass was attached.
12. The resulting product was dried overnight.

(v) Immunostaining

Immunostaining was performed as follows.

1. A circle was drawn around the section with a PAP pen.
2. An FBS solution (1% PBS) was added dropwise to the inside of the circle drawn with the PAP pen and allowed to stand for 1 hour for blocking.
3. The resulting product was placed in a staining bottle such that the section was not peeled off, followed by washing with PBS.

4. A primary staining solution was added dropwise to the inside of the circle drawn with the PAP pen and allowed to stand for 1 hour.
5. The resulting product was placed in a staining bottle such that the section was not peeled off, followed by washing with PBS.
6. A secondary staining solution was added dropwise to the inside of the circle drawn with the PAP pen and allowed to stand for 1 hour.
7. The resulting product was placed in a staining bottle such that the section was not peeled off, followed by washing with PBS.
8. DAPI was added dropwise.
9. A cover glass was placed on.
10. Observation was conducted from the cover glass side.

The three-dimensional muscle tissue prepared according to the present invention is characterized by being oriented.

The orientation index of the three-dimensional muscle tissue was evaluated as follows using two-dimensional Fourier transform.

1. The image was cut so that the length and width are power of 2 pixels.
2. The image was grayed.
3. The Hanning window was used.
4. Two-dimensional Fourier transform was applied using the fft2 function of a numerical analysis software (MATLAB (registered trademark), provided by The MathWorks, Inc.).
5. The 2D Fourier transform image was integrated in polar coordinates, and the pixel values from 1 degree to 180 degrees were added.
6. Each value from 1 degree to 180 degrees was divided by the sum of these values to obtain the average.

Furthermore, nuclei were identified in the HE-stained images using image processing software (ImageJ, open source), and the number of nuclei were counted as follows.

1. The images were combined using Make composite.
2. The image were converted to 32-bit RGB color using RGB Color values.
3. The RGB color image was split for HE using Deconvolution.
4. The threshold was applied to the blue image to separate the image containing the nuclei from the background.
5. The connected nuclei was separated using Watershed.
6. The number of nuclei was counted.

(III) Evaluation (1) Evaluation of Device

The shape of the channels 3 and the flow in the channels 3 were confirmed.

(1-1) Shape of Channels 3

A gel structure without cells was produced using a collagen gel as the hydrogel and using the nine-support-member array shown in FIG. 4. The hydrogel was injected into the culture space 2 and allowed to stand. After gelation, acupuncture needles 10 as the channel-foaming members were pulled out, and the cross-section perpendicular to the channels was immediately cut. To prevent the channels from being broken during cutting, an alginate gel solution was passed through the channels and formed into a gel so that the channels retained their shape. The observation of the cut surface confirmed nine holes. It was thus confirmed that the formation of channels was possible by removing the needles after gelation.

(1-2) Flow of Culture Medium in the Channels 3

To confirm that the channels were not blocked, ink was allowed to flow through the channels.

Specifically, with support members, a gel structure without cells was produced using a collagen gel, and blue ink was allowed to flow immediately after gelation. The appearance of flow was recorded on video through a microscope (STZ-171, Shimadzu Corporation).

Figure 9:
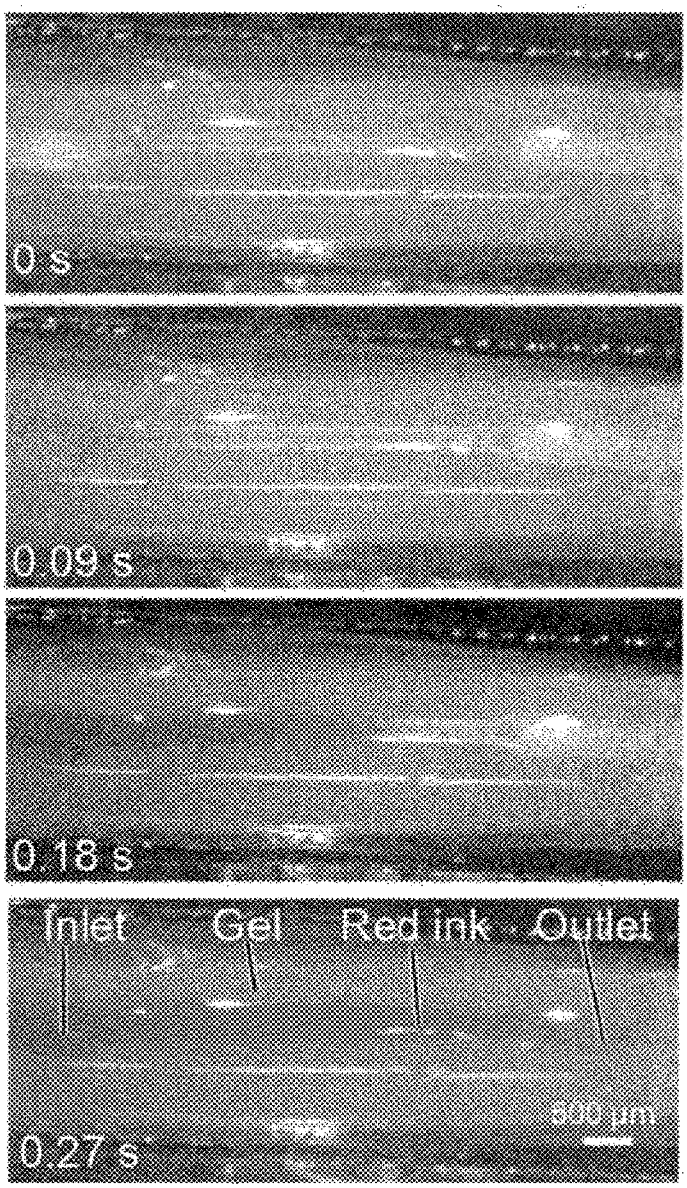
FIG. 9 is images of ink flow in the channels.

As shown in FIG. 9, the flow of ink in the channels was confirmed.

This clarified that delivering a culture medium that contains oxygen and nutrients into the interior of the three-dimensional muscle tissue is possible.

(2) Vertical Culture and Parallel Culture

First, the difference between vertical culture and parallel culture is explained. In the case of parallel culture, when 100% collagen gel was used, an alginate gel poured from the culture medium inlet 6 after 7 days of culture was discharged from the culture medium outlet 7. However, when a gel mixture of collagen gel and matrigel (collagen gel:matrigel=50%:50%) was used, an alginate gel poured from the culture medium inlet 6 after 7 days of culture was not discharged from the culture medium outlet 7. This is presumably because the channels were blocked during the 7 days of culture since matrigels are softer than collagen gels and thus easily cause deformation of the structure by gravity.

In the case of vertical culture, the direction of gravity is the same as that of the channels, making it less likely to cause blockage of the channels; thus vertical culture is more suitable than parallel culture. The details are described later.

Figure 10:
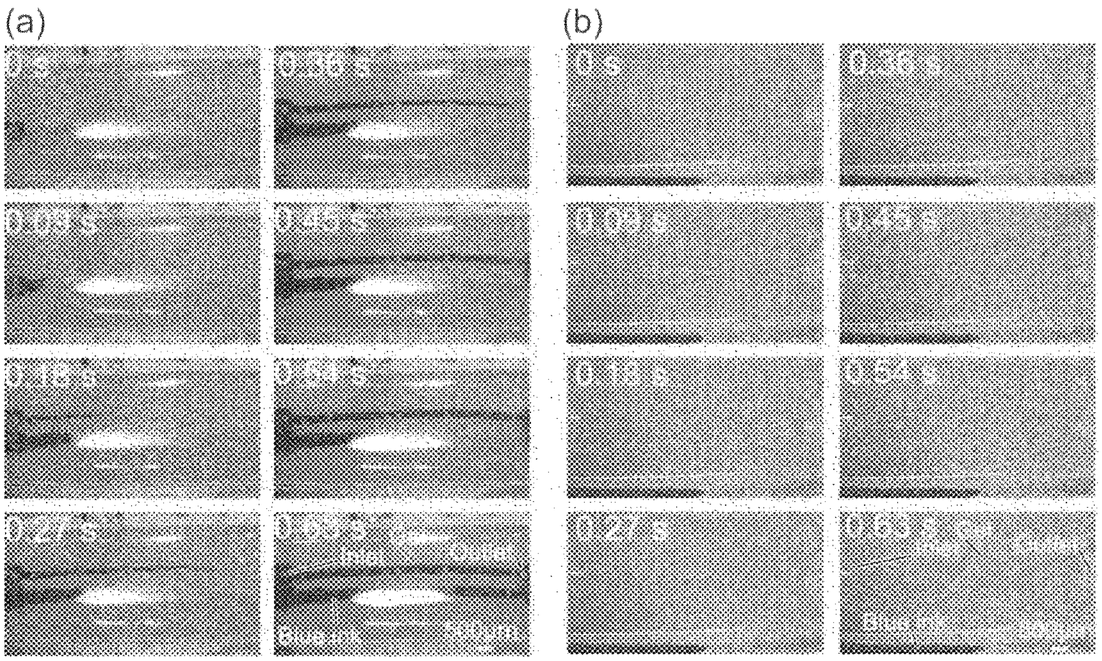
FIG. 10 is images for comparison of the ink flow. (a): vertical culture, (b): parallel culture.

A gel structure was produced in the same manner as described above using a four-support-member array and using a cell-free hydrogel obtained by mixing a collagen gel and matrigel in a ratio of 1:1. The resulting gel structure was placed in DMEM medium and cultured in an incubator for 1 day. FIG. 10 shows the results of ink flow in the channels 3 in vertical culture and parallel culture.

As shown in FIG. 10(*a*), ink flow in the channels was observed in vertical culture. As shown in FIG. 10(*b*), however, ink flow was not observed in parallel culture. In the four-support-member array, the support members were arranged in 2 columns and 2 rows; thus, two channels were observed under a microscope from the top surface. Given this, the images in (a) show the flow in at least one channel in different columns. In the images in (b), the four channels 3 are all believed to have been blocked.

These results suggest that the ink flow observed at the bottom of the images of parallel culture was due to the ink that could not flow into the channels from the culture medium inlet 6 and thus leaked out from the gap between the support members and the gel. Focusing on the support member on the lower side of 0.09 S and 0.18 S images in (b), it is confirmed that bubbles accumulated inside the support member were about to flow into the channel but unable to do so. This is presumably because the channel was blocked.

Parallel Culture

The results of parallel culture using 100% collagen gel are described here. The purpose of this experiment is to show that culture of muscle tissue is possible even by parallel culture if a collagen gel is used alone. In this experiment, when an alginate gel was allowed to flow into the channels after 7 days of culture, red culture medium, which was assumed to have remained in the channels, was pushed out from the opposite side of the channels, indicating that the channels remained open.

Shrinkage of Muscle Tissue

Figure 11:
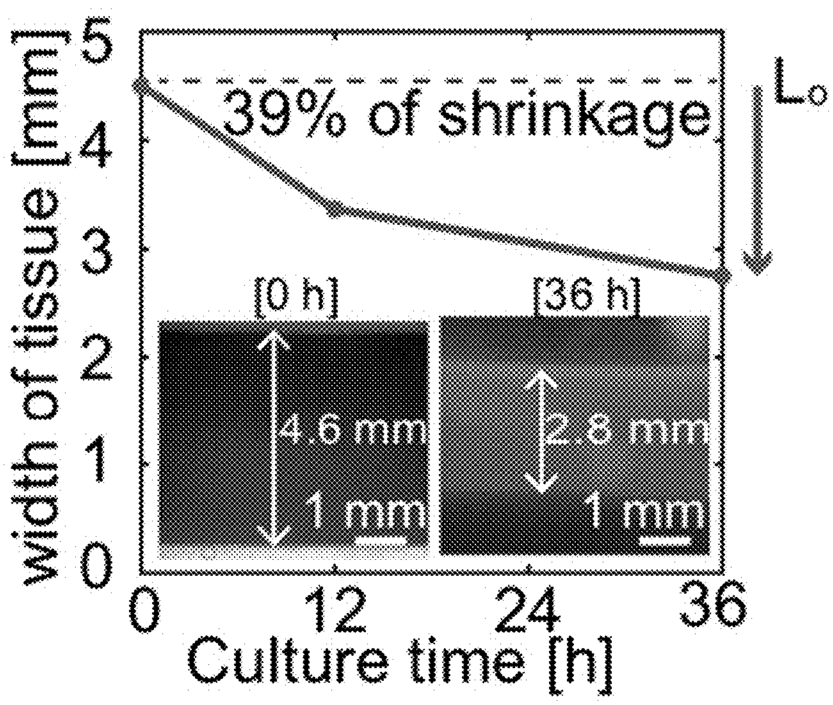
FIG. 11 is a graph showing the change in the degree of shrinkage up to 36 hours.
Figure 12:
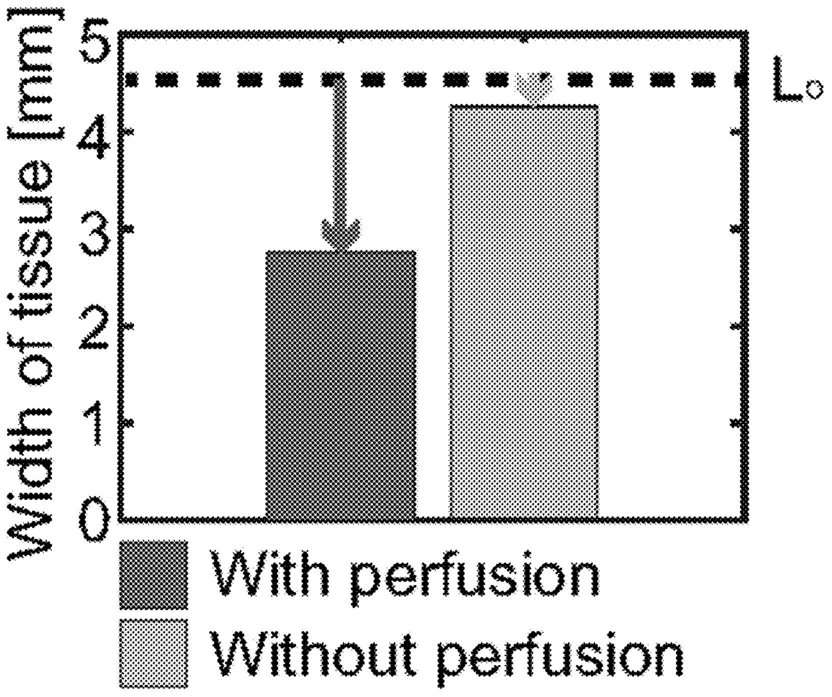
FIG. 12 is a graph comparing the degrees of shrinkage between with and without perfusion after 36 hours.

The degree of spontaneous shrinkage of tissue during culture was confirmed to vary depending on whether the tissue was with or without perfusion. Specifically, after 36 hours of culture, the tissue with perfusion showed 39% shrinkage in width compared to the original (FIG. 11). Further, the percentage of shrinkage was greater with perfusion than without perfusion (FIG. 12). These results reveal that the cells were more active with perfusion, which showed a greater percentage of shrinkage, than without perfusion.

Figure 13:
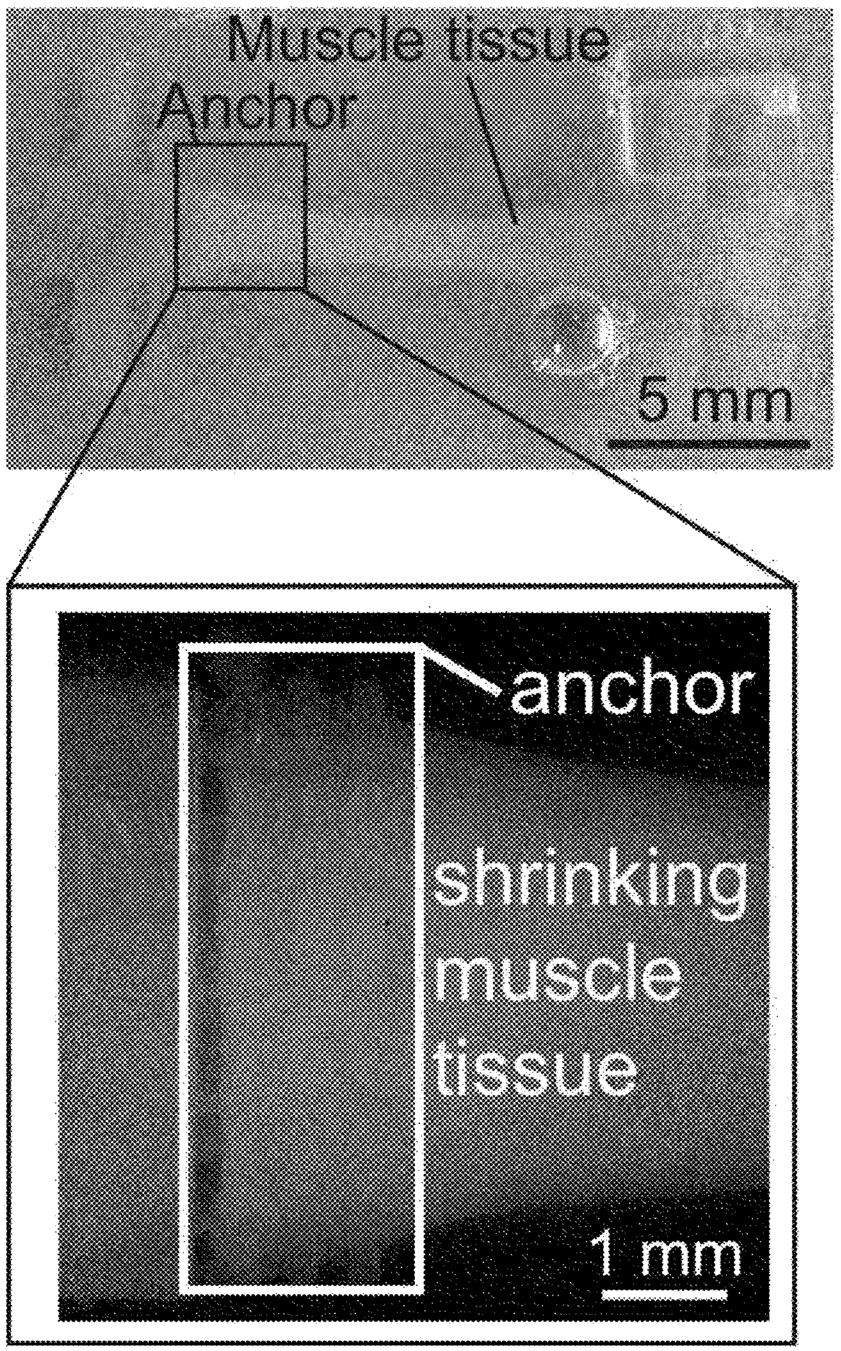
FIG. 13 is images showing a shrinking muscle tissue anchored after 36 hours.

FIG. 13 is a photo showing the tissue after 36 hours encapsulated in an alginate gel, and a magnified photo of the region of the meshed anchor 11. These photos show that the muscle tissue was anchored even when tension was applied to the tissue to undergo 39% shrinkage in width.

Orientation Index of Muscle Tissue

Figure 14:
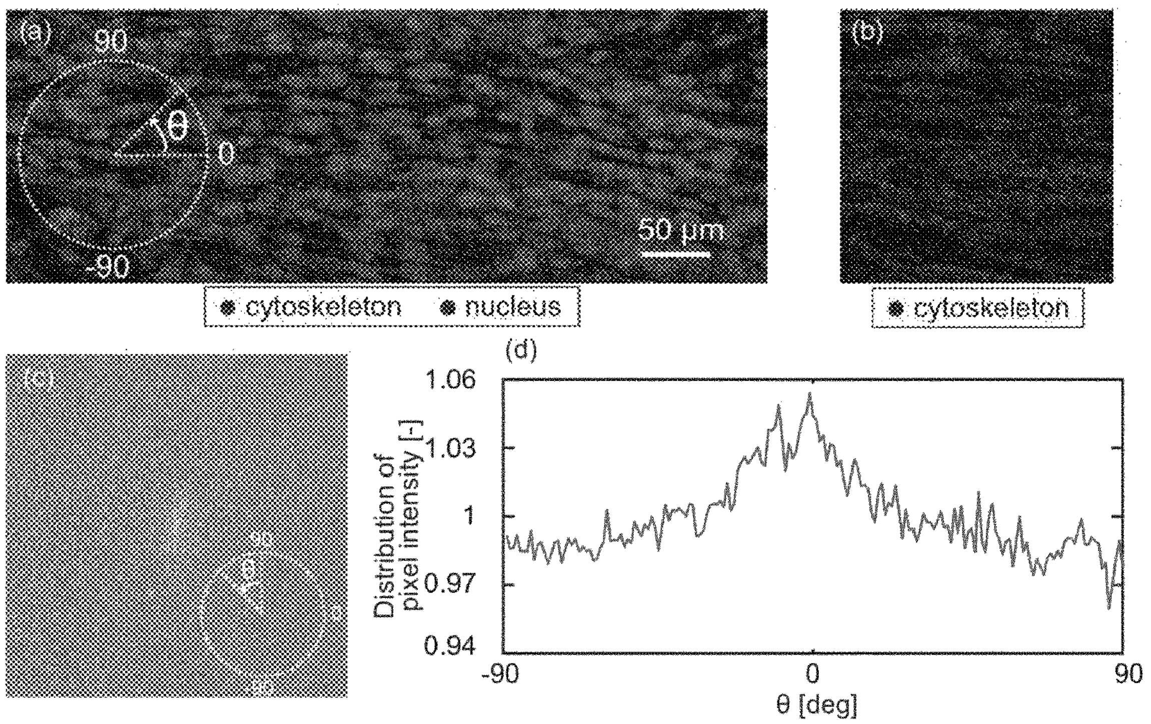
FIG. 14 is images and a graph in terms of the orientation index of a muscle tissue after 152 hours. (a) is a fluorescent staining image of the muscle tissue, (b) is an image showing calculated orientation, (c) is an FFT image, and (d) is a graph showing distribution of the cell extension direction.

To confirm the orientation index of the muscle tissue, the periphery of the muscle tissue was stained with a fluorescent dye for observation. FIG. 14(*a*) is a fluorescent staining image of a region in contact with the medium of the muscle tissue after 152 hours of culture with perfusion. Red represents phalloidin-stained actin filaments, and blue represents nuclei stained with Hoechst. Many nuclei are observed on a single myotube, indicating that myoblasts have fused. FIG. 14(*d*) is an image showing the directional distribution of actin from the image of actin filaments alone. The muscle tissue was confirmed to be oriented in the direction of 0 degrees since a peak was observed at 0 degrees.

Figure 15:
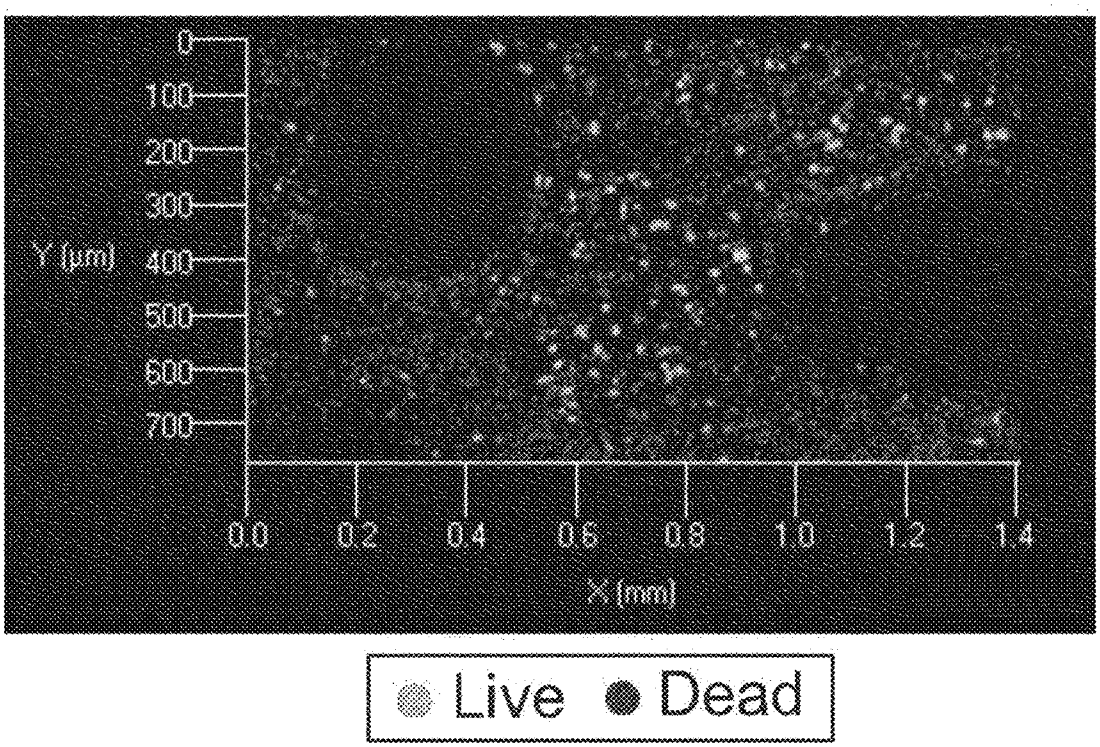
FIG. 15 is a fluorescent staining image based on live/dead assay between the channels.

Viability at the Cross-Section of the Muscle Tissue Perpendicular to the Channels After 36 hours of culture, the muscle tissue was cut and subjected to live/dead assay. FIG. 15 shows the results of observation under confocal microscope. The cells are assumed to die on the cut surface; thus, the interior of the tissue that was 34 μm away from the cut surface was observed. The observation confirmed that 196 cells were viable while 725 cells were dead, indicating that the viability was as low as 21%. A possible reason for the low cell viability was damage caused during the process of cutting the tissue. Although observation was made at the interior of the tissue that was 34 μm away from the cut surface, the tissue may have possibly been pulled during the cutting process, causing the cells to be damaged.

Another characteristic result was that more viable cells were present between the channels while more dead cells were present around the channels. The lack of oxygen in culture is a possible cause of cell death. In this case, cells closer to the channels should be viable, and dead cells should increase as the distance from the channels increase; however, the trend here was the opposite. This suggests that the cells did not die during the culture period, but that the cells around the channels were damaged and died when the acupuncture needles were pulled out to foam the channels. Since the needles were coated with BSA, cell adhesion to the needles was unlikely to occur. However, the cell death was possibly caused due to rubbing when the needles were removed. To avoid this, the needles must be removed slowly.

Vertical Culture

To confirm whether the support members 8, 9 and the anchors 11 function in vertical culture, the appearance of the cells after culture was observed using HE staining and fluorescent immunostaining images.

Figure 16:
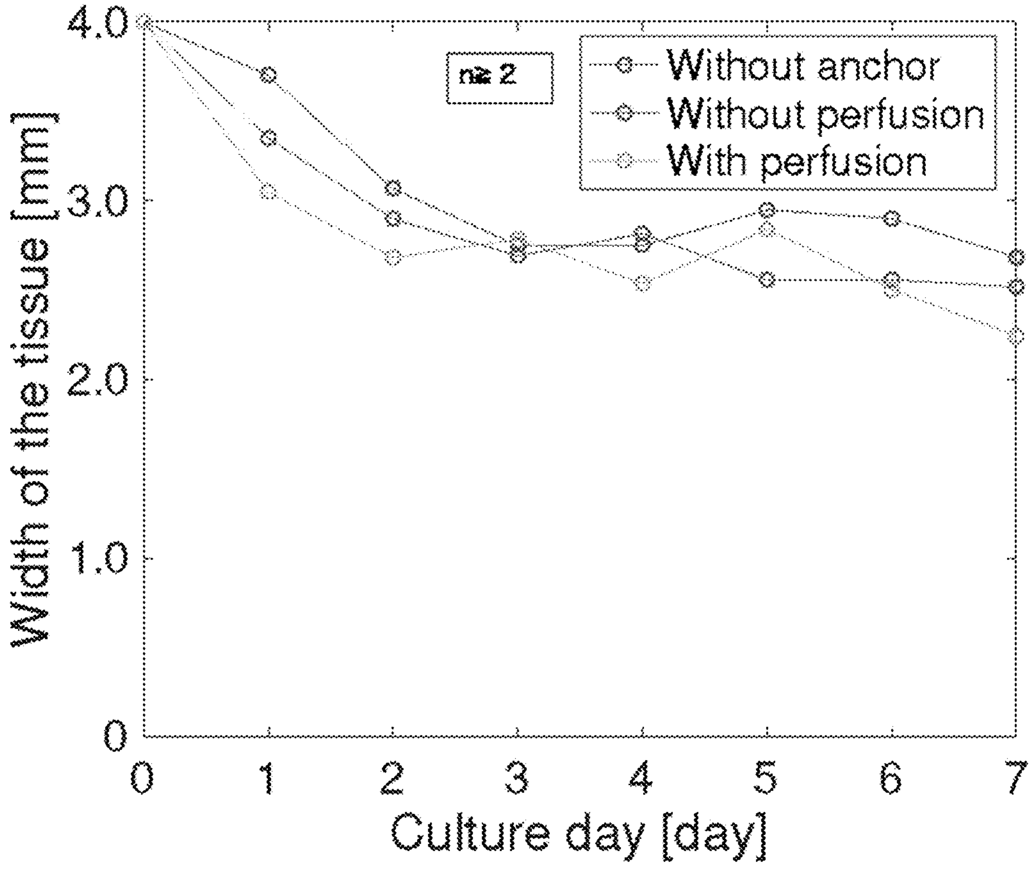
FIG. 16 is a graph showing the change in the degree of shrinkage.

Muscle tissue has properties of shrinking during culture and thus must be anchored. FIG. 16 is a graph showing the change in width during culture without shaking. The tissue with anchors and with perfusion, the tissue with anchors and without perfusion, and the tissue without anchors and without perfusion are respectively referred to as "with perfusion" (below, "w/perfusion"), "without perfusion" (below, "w/o perfusion"), and "without anchor" (below, "w/o anchor"). The width was observed by observing the side, i.e., the curved surface, of the tube through a camera (VW-600C, Keyence Corporation). The length was calculated based on a reference length of the support member array with anchors. The experiment showed the following two results.

(i) The percentage of shrinkage after 7 days of culture increased in the following order: w/perfusion, w/o perfusion, and w/o anchor.

(ii) In some samples of w/o perfusion, the muscle tissue fell off from the support members.

The results in (i) above can be explained according to the number of viable cells. It is well known that muscle tissue shrinks during the culture period. The shrinkage occurs due to the traction of the cells reorganizing the extracellular matrix.

Due to the effect of perfusion, it is believed that more cells were alive in the tissue w/perfusion than in the tissue w/o perfusion; thus, the amount of cells involved in shrinkage was also believed to be greater in the tissue w/perfusion. It is thus believed that the degree of shrinkage in width was greater in the tissue w/perfusion than the tissue w/o perfusion.

Next, the order, i.e., w/o perfusion and then w/o anchor, was believed to be due to the difference between presence and absence of displacement in the vertical direction. Between the tissue w/o perfusion and the tissue w/o anchor, the presence or absence of the anchors made a difference in the degree of shrinkage in width. The tissue with anchors (w/o perfusion) showed no displacement in the vertical direction, while the tissue w/o anchor showed displacement at the edge of the tissue even to the tip of the support members. Without the effect of perfusion, the percentages of shrinkage would have been the same between these two; however, presumably, due to the presence of displacement in the vertical direction, the tissue w/o anchor resulted in a smaller degree of shrinkage in width.

Figure 17:
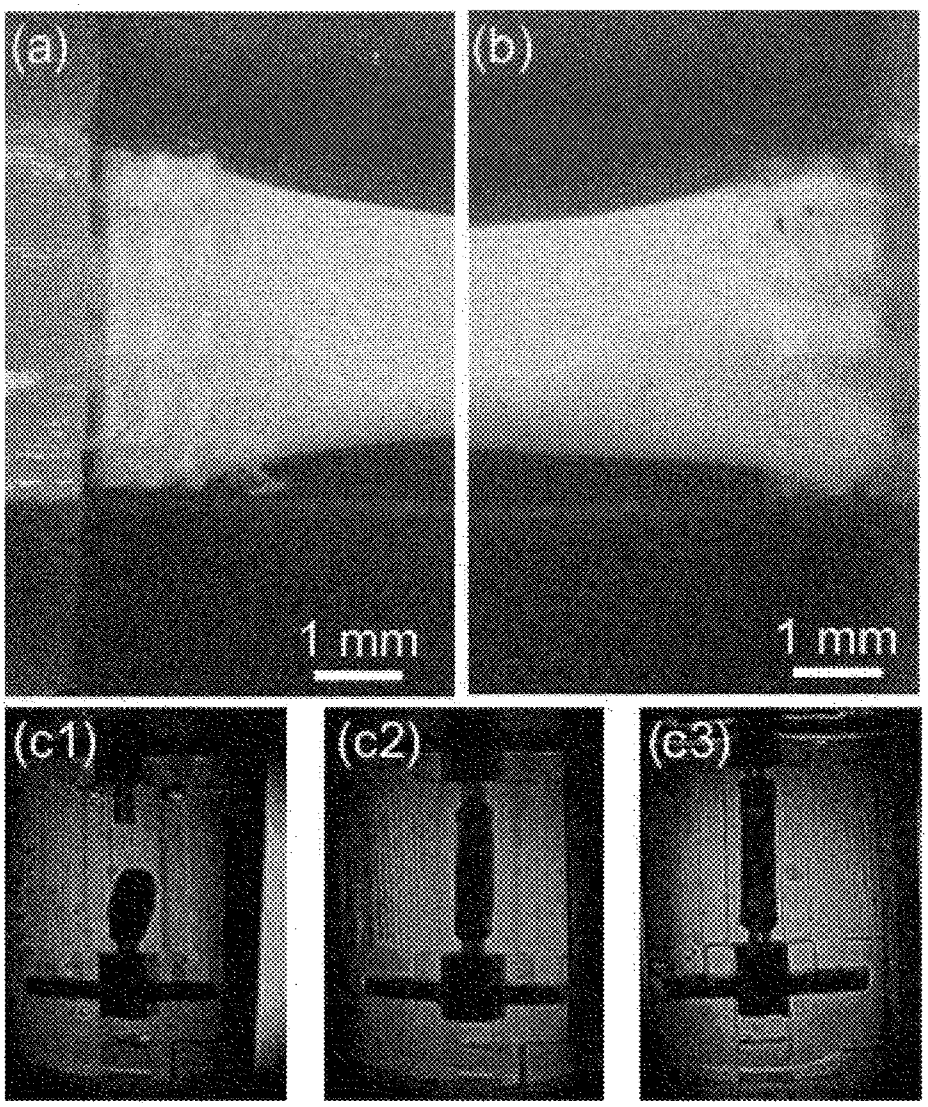
FIG. 17 is images showing an anchored tissue after 7 days of culture. (a) and (b) are images showing support member arrays at both ends, (c1) is an image showing a muscle tissue that has fallen off after 7 days of culture without anchors, (c2) is an image showing a muscle tissue about to fall off after 7 days of culture without anchors, and (c3)) is an image showing a muscle tissue about to fall off after 7 days of culture without anchors.

Regarding (ii) above, as shown in FIGS. 17(*a*) and (*b*), the tissue w/perfusion was fixed to the anchors after 7 days of culture. However, as shown in FIG. 17(*c*1), some samples of tissue without anchors fell off from the support members during 7 days of culture. Not all of the samples fell off; as shown in FIG. 17(*c*2), a sample showed shrinkage of the muscle tissue to the tip of the support members and was about to fell off, and the other showed only a small degree of shrinkage. None of the muscle tissues with anchors was detached from the anchors.

These results indicate that the anchors 11 prevent the muscle tissue from falling off in the device of the present invention for culturing a contractile muscle tissue.

Channels after Culture

Figure 18:
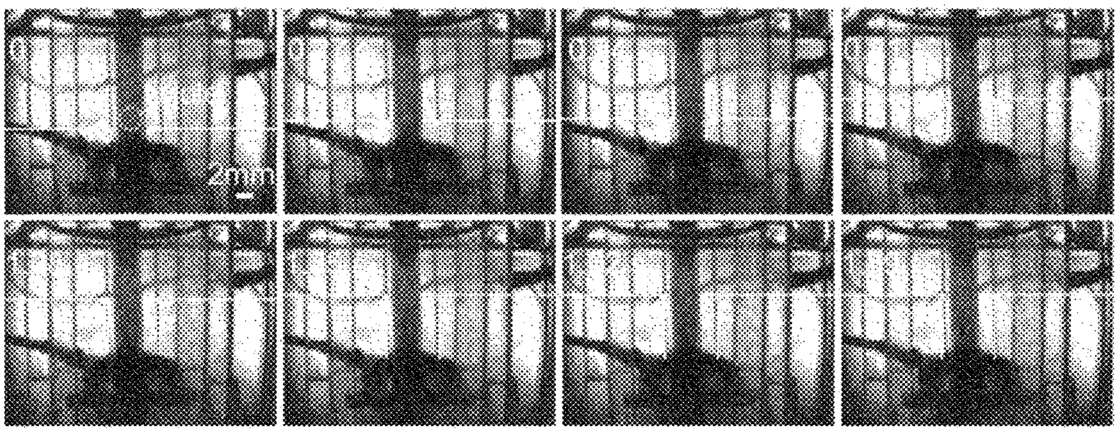
FIG. 18 is images showing channels after culture. The sampling time was 0.27 seconds.
Figure 19:
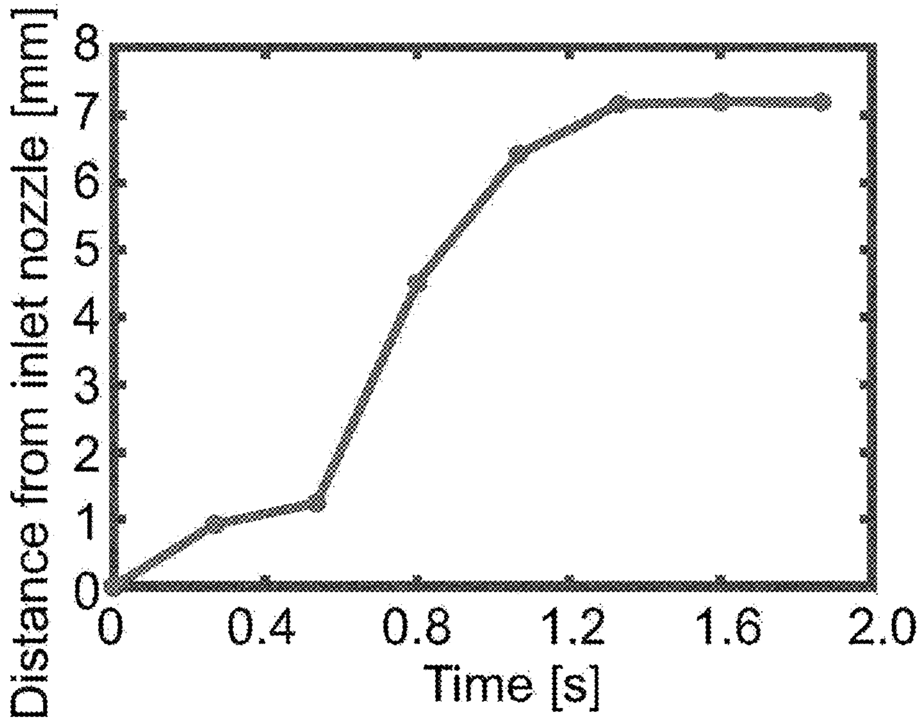
FIG. 19 is a graph showing the ink transfer distance.

Whether the channels 3 remained open after culture even when shrinkage occurred, and whether the culture medium was perfused, were confirmed by allowing ink to flow. After 7 days of culture, ink was allowed to flow from the bottom to the top of the channels 3 using the tube through which a culture medium had been flowing (FIG. 18). The white horizontal lines at 0 s in FIG. 18 are the start lines of the support members in the tissue. The solid white lines show the location of the ink, and the length of the arrows represents the distance the ink flowed. FIG. 19 is a graph constructed by plotting the time on the horizontal axis. Although four channels were present in the tissue, only two channels should actually be visible since the channels were overlapped. Of the two, however, only one channel was visible, suggesting that the channel was broken during the process, and thus no ink flowed. Although it is assumed that the flow distance would increase linearly with time, this did not apply to the obtained results (FIG. 19). This is presumably because of the leakage of ink from the hole at the lower part of the tissue shown in FIG. 18. That is, it is presumed that the flow pressure was weakened due to the presence of the hole, making ink unable to flow up to the top.

Long-Side Section

Figure 20:
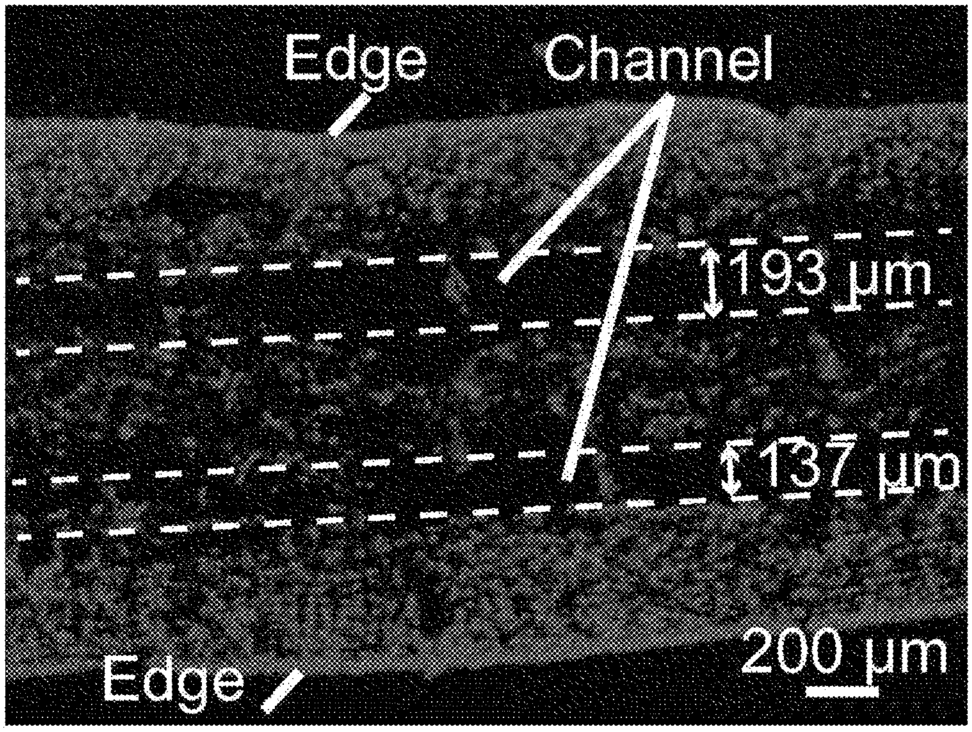
FIG. 20 is an image of the long side of a frozen section with nuclei stained with Hoechst.

The presence of channels was also confirmed in a long-side section prepared using a cryostat from a sample different from that mentioned above (FIG. 20). Although the channels were present in 2 columns and 2 rows in the muscle tissue sample, only two channels were present in one plane. The widths of the channels were 193 μm and 137 μm. The difference in the width is presumably because shrinkage occurred unevenly during culture.

Uneven Distribution of Nuclei Throughout the Tissue

Figure 21:
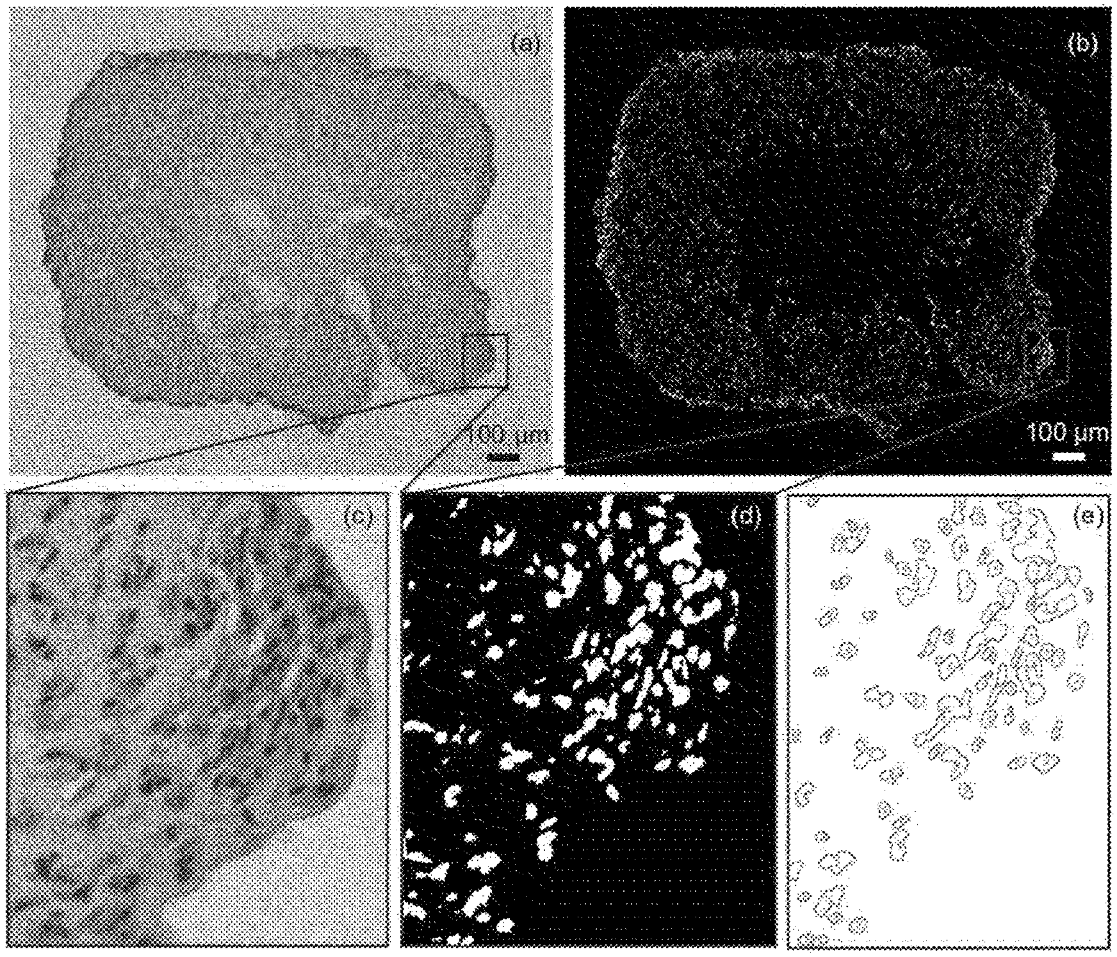
FIG. 21 shows HE staining and image processing. (a) is an HE staining image when perfusion failed, (b) is an image after binarization, (c) is an image showing the region in which nuclei are densely packed in the periphery of a sample, (d) is a binarized image of (c), and (e) is a count image.

An 8-μm-thick section was prepared parallel to the cross-section perpendicular to the channels, and HE staining was performed. The reason that the nuclei were not present in the center is explained here. FIG. 21(*a*) is an HE staining image. The ink flow experiment confirmed that this sample failed perfusion, and in this sample, the absence of nuclei at the center was confirmed. The absence of nuclei is presumed to be either because denucleation occurred, resulting in the absence of nuclei, or because nuclei have moved closer to the periphery in search of culture medium. In particular, in the periphery in which the nuclei are densely packed as shown in FIG. 21(*c*), multiple nuclei are easily counted as a single nucleus; thus, the threshold was carefully determined. The threshold was determined to be that shown in FIG. 21(*d*), and counting was performed as in FIG. 21(*e*).

From the binarized image in FIG. 21(*b*), 10800 nuclei were confirmed. Since the area was 1291152 $\mu m^2$ (1.3 $mm^2$), the nuclei were present at a density of 8300 cells/$mm^2$. Further, since the thickness of the section was 8 μm, the cell concentration was calculated to be $10^9$ cells/ml. However, nuclei would be double-counted when present in the plane between one section and the next section. Thus, calculation was performed again, assuming that the nucleus size was 8 μm; the cell concentration was $50\times10^7$ cells/ml (half of the calculated value of $10^9$ cells/ml).

On the other hand, the initial cell concentration of the sample used in this experiment was $4.0\times10^7$ cells/ml. Considering that the cross-section (16 $mm^2$) shrank to about 1.3 $mm^2$, the cell concentration would be $49\times10^7$ cells/ml.

Accordingly, the cell concentration based on actual measurement and the cell concentration estimated from the initial cell concentration of the sample are almost the same, suggesting that the nuclei at the center have moved.

Figure 22:
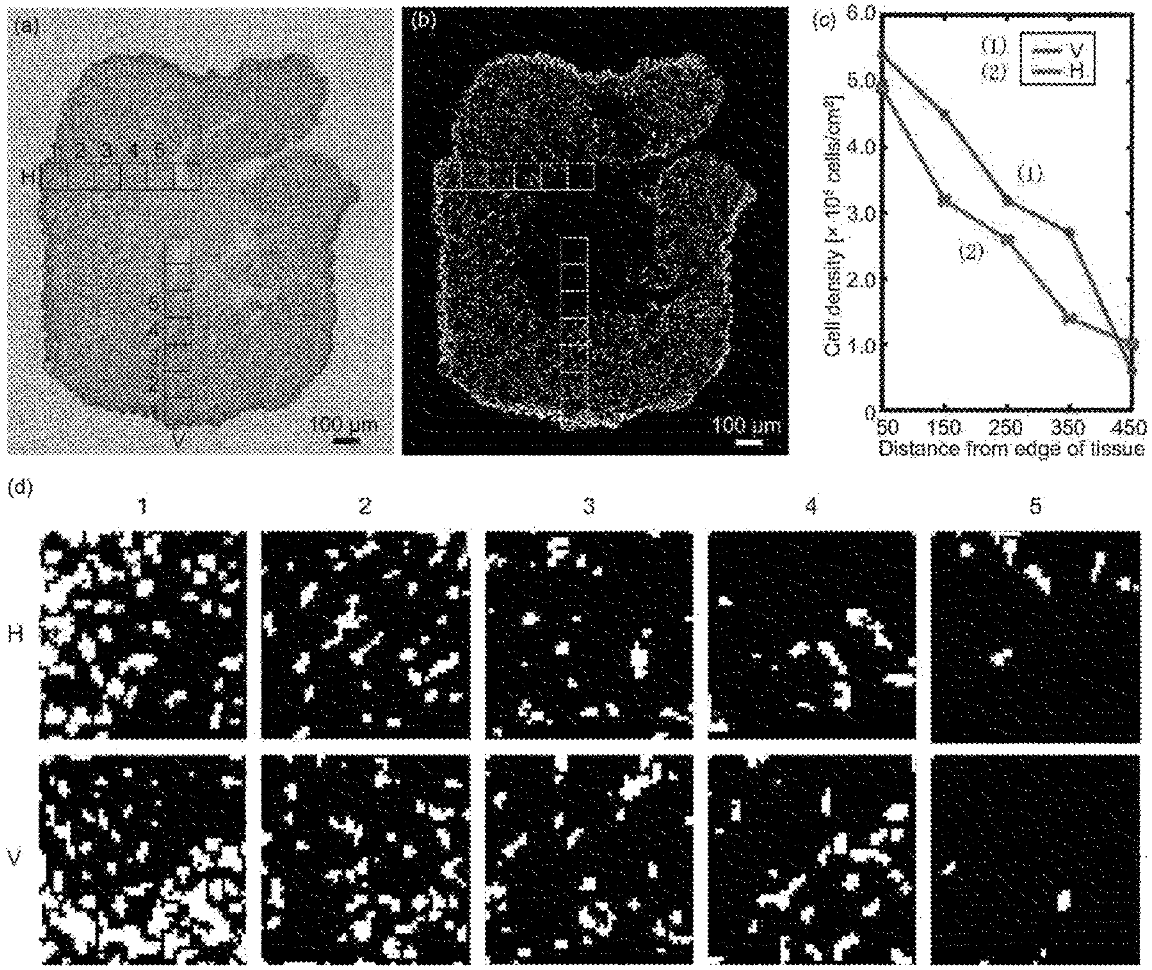
FIG. 22 shows HE staining and image processing. V and H represent the vertical and horizontal directions, respectively. (a) is an HE staining image when perfusion failed without shaking, (b) is an image after binarization, (c) is a graph comparing the cell concentrations, and (d) is images used in (c).

Next, FIG. 22(*c*) shows a linearly decreasing relationship between the distance from the surface of the cellular tissue to the center and the decrease in the cell concentration. This is presumably because when oxygen is supplied only from the periphery of the tissue, oxygen is consumed by the cells on the outer side, and so the oxygen concentration decreases toward the center.

Figure 23:
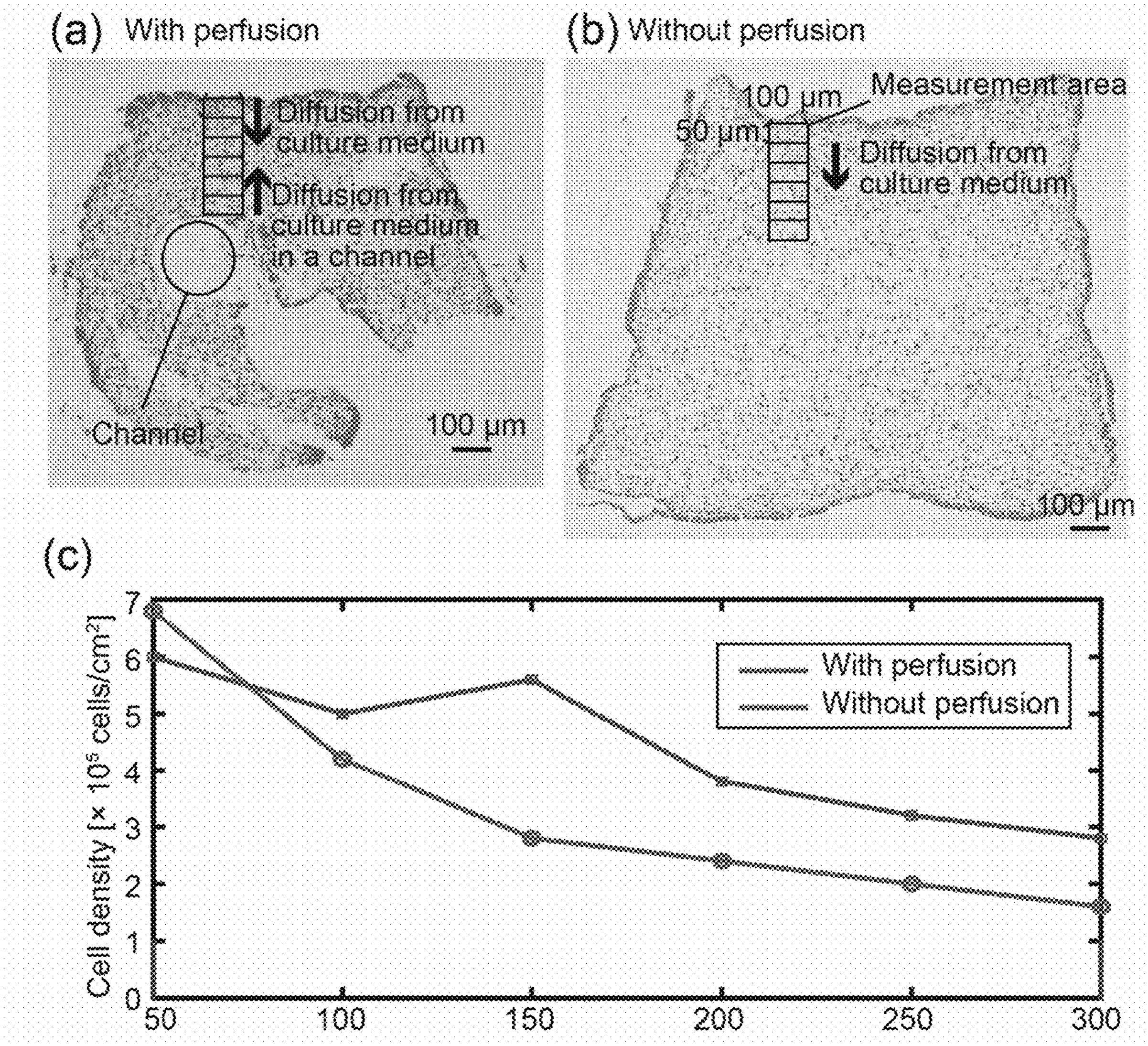
FIG. 23 is HE staining images. (a) is an image of a tissue obtained with perfusion, (b) is an image of a tissue obtained without perfusion, and (c) is a graph comparing the cell concentrations.

Relationship Between the Distance from the Interface Between the Tissue and Culture Medium and the Cell Concentration The cell concentrations were compared between the muscle tissue sample with perfusion and the muscle tissue sample without perfusion (FIG. 23). FIG. 23(*a*) shows a sample with perfusion, and FIG. 23(*b*) shows a sample without perfusion. FIG. 23(*a*) shows the presence of a hole. The cell concentrations in the rectangular (100 μm×50 μm) regions were compared between these samples (FIG. 23(*c*)). The results revealed that both of the samples showed a decrease in the cell concentration with an increase in the distance from the edge of the tissue; however, the sample with perfusion showed a moderate decrease in the cell concentration. This is presumably because oxygen and nutrients were also supplied from the interior by perfusion.

Dense Nuclei when Perfusion Succeeded

Figure 24:
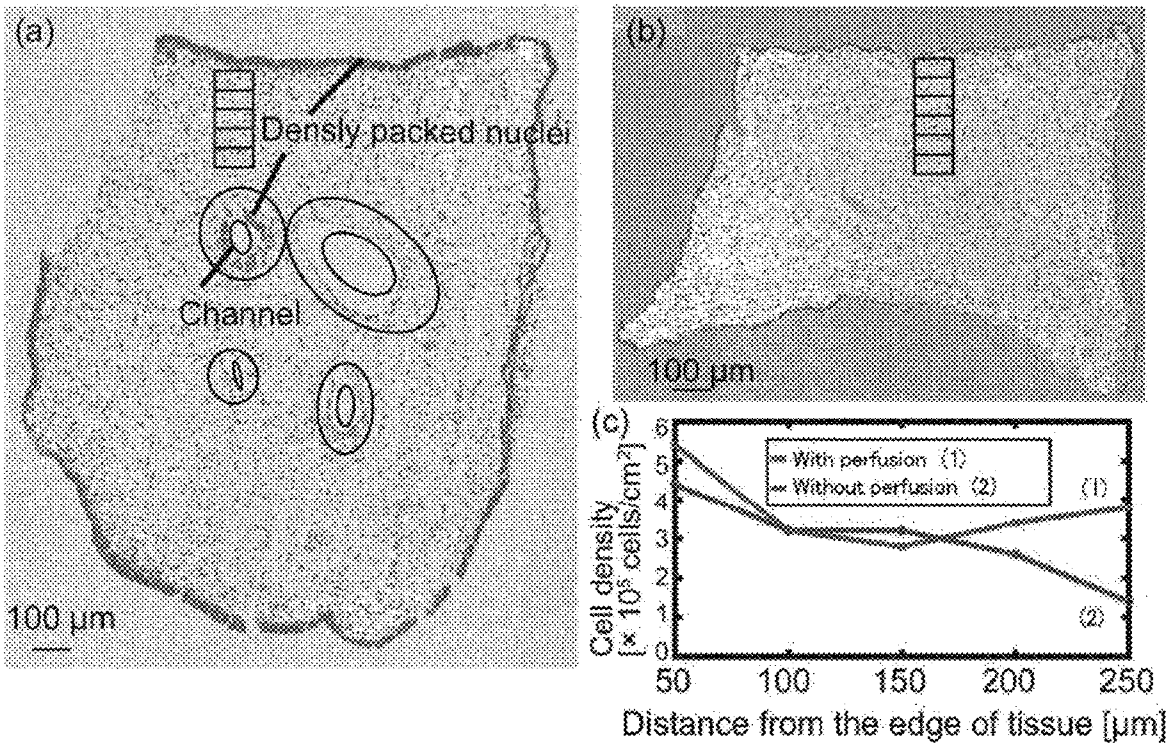
FIG. 24 is HE staining images showing densely packed nuclei around the channels after successful perfusion. The regions enclosed by two ellipses represent the edges of the channels at which nuclei are densely packed. (a) is an image of a tissue obtained with perfusion, (b) is an image of a tissue obtained without perfusion, and (c) is a graph comparing the cell concentrations.

In the sample in which perfusion succeeded, the nuclei were densely packed around the channels (FIG. 24(*a*)). The sample without perfusion (FIG. 24(*b*)) showed a trend of a decrease in the cell concentration with an increase in the distance from the outer periphery of the muscle tissue, while the sample with perfusion showed an increase in the cell concentration with a decrease in the distance from the channels (FIG. 24(*c*)). This is presumably because a culture medium that contained oxygen and nutrients as sufficient as in the tissue periphery was delivered.

Orientation Index of Muscle Tissue

Figure 25:
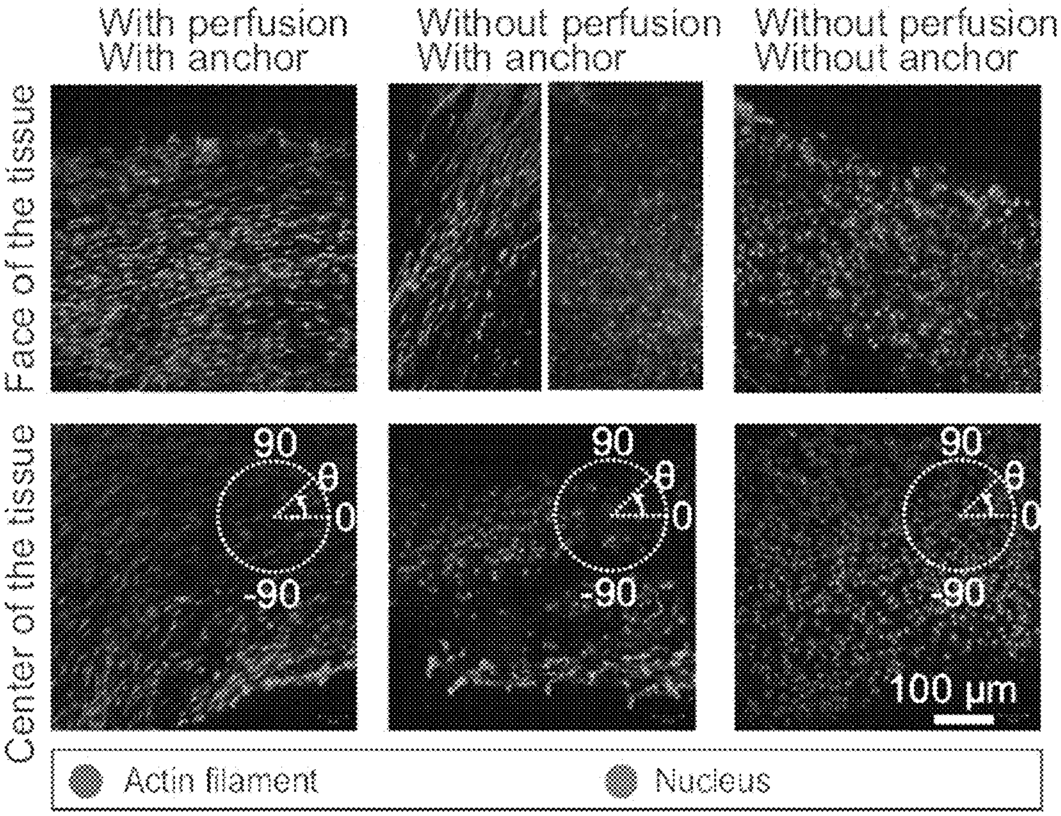
FIG. 25 is photos of the face and interior of the tissue.
Figure 26:
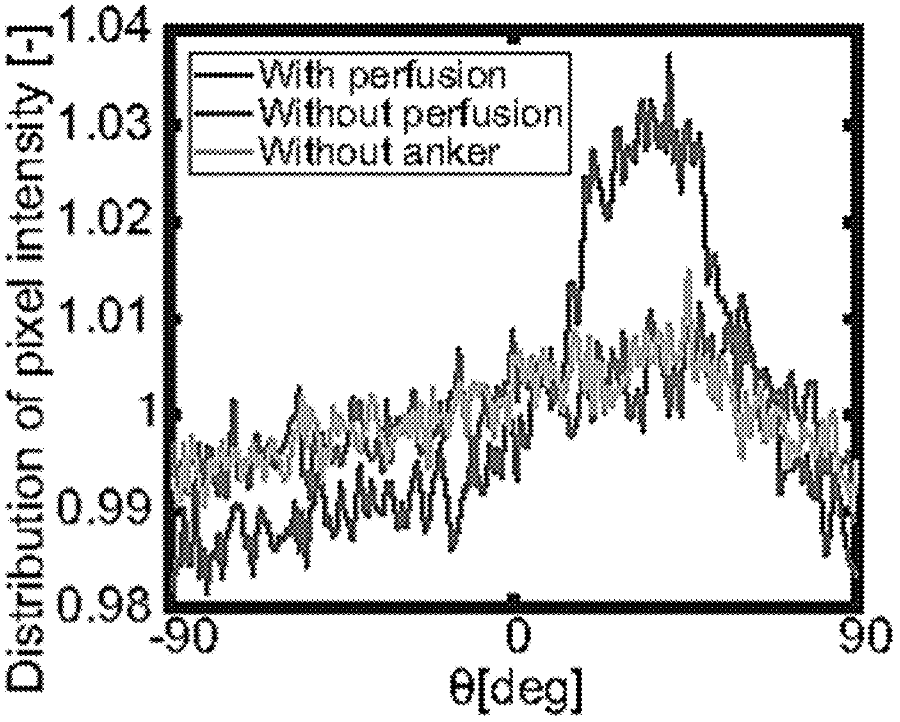
FIG. 26 is a graph showing orientation indices in terms of the interior of the tissue.

The orientation index of actin filaments of the tissue cultured for 8 days without shaking was studied. The images in the upper row of FIG. 25 show actin filaments and nuclei stained on the surface of the tissue. The images in the lower row show actin filaments and nuclei stained in the interior of the tissue. The results of the sample w/perfusion, the sample w/o perfusion, and the sample w/o anchor are shown in both the upper and lower rows. FIG. 26 is a graph showing the orientation index of the actin filaments of the samples in the lower row. The results indicate that the sample with anchors and with perfusion (with perfusion) was a muscle tissue with a high orientation index.

DESCRIPTION OF THE REFERENCE NUMERALS

1 Device for constructing a three-dimensional muscle tissue
2 Culture space
3 Channel
4 First connector
5 Second connector
6 Culture medium inlet
7 Culture medium outlet
8 First support member
9 Second support member
10 Channel-forming member
11 Muscle tissue anchor
12 Pump
13 Skeletal myoblast
14 Nutrients etc.
15 Culture medium
16 Muscle tissue
17 Substrate
18 Side wall
19 Opening (formed in the first connector and/or the second connector)
20 Sealing material

The invention claimed is:

1. A device for constructing a three-dimensional muscle tissue, comprising a culture tank having a culture space, a first connector and a second connector provided at positions opposite to each other within the culture space, a culture medium inlet provided at the first connector, a plurality of first support members that are provided at the first connector and from which culture medium introduced from the culture medium inlet is enabled to be discharged, a plurality of second support members that are provided at the second connector and into which culture medium is enabled to flow, a mesh-like first muscle tissue anchor engaged to the first support members and/or the first connector, and a mesh-like second muscle tissue anchor engaged to the second support members and/or the second connector.

2. The device for constructing a three-dimensional muscle tissue according to claim 1, further comprising channel-forming members for culture medium that are engaged to the first support members and the second support members.

3. The device for constructing a three-dimensional muscle tissue according to claim 1, further comprising a pump for supplying culture medium to the culture medium inlet.

4. A method for producing a three-dimensional muscle tissue, the method comprising, in the device for constructing a three-dimensional muscle tissue of claim 2, filling the culture space between the first connector and the second connector with a hydrogel containing skeletal myoblasts, with the channel-forming members being inserted into the first support members and the second support members, removing the channel-forming members after the hydrogel is solidified, and supplying culture medium from the culture medium inlet through the first support members to the second support members to three-dimensionally culture the skeletal myoblasts.

* * * * *